United States Patent
Hastings et al.

(10) Patent No.: US 9,192,790 B2
(45) Date of Patent: Nov. 24, 2015

(54) FOCUSED ULTRASONIC RENAL DENERVATION

(75) Inventors: Roger Hastings, Maple Grove, MN (US); Allan C. Shuros, St. Paul, MN (US); Frank Ingle, Palo Alto, CA (US); Mark A. Hollingsworth, Bloomington, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 207 days.

(21) Appl. No.: 13/086,116

(22) Filed: Apr. 13, 2011

(65) Prior Publication Data
US 2011/0257523 A1 Oct. 20, 2011

Related U.S. Application Data

(60) Provisional application No. 61/324,164, filed on Apr. 14, 2010.

(51) Int. Cl.
*A61B 8/00* (2006.01)
*A61N 7/02* (2006.01)
*A61B 8/08* (2006.01)
(Continued)

(52) U.S. Cl.
CPC .............. *A61N 7/022* (2013.01); *A61B 8/0891* (2013.01); *A61B 8/12* (2013.01); *A61B 8/4488* (2013.01); *A61B 18/0206* (2013.01); *A61B 2018/00404* (2013.01); *A61B 2018/00434* (2013.01); *A61B 2018/00511* (2013.01);
(Continued)

(58) Field of Classification Search
CPC ........... A61N 7/022; A61N 2007/0095; A61N 2007/003; A61B 8/4488; A61B 8/12; A61B 8/0891; A61B 18/0206; A61B 2018/00434; A61B 2018/00404; A61B 2018/00511; A61B 2019/528
USPC .......................... 600/439, 471; 601/3; 606/27
See application file for complete search history.

(56) References Cited

U.S. PATENT DOCUMENTS

| 164,184 A | 6/1875 | Kidder |
|---|---|---|
| 1,167,014 A | 1/1916 | O'Brien |

(Continued)

FOREIGN PATENT DOCUMENTS

| DE | 10038737 A1 | 2/2002 |
|---|---|---|
| EP | 1053720 A1 | 11/2000 |

(Continued)

OTHER PUBLICATIONS

Gentry et al., "Combined 3D Intracardiac Echo and Ultrasound Ablation", Medical Imaging 2003: Ultrasonic and Signal Processing, vol. 5035, 2003, pp. 166-173.

(Continued)

*Primary Examiner* — Jonathan Cwern
(74) *Attorney, Agent, or Firm* — Kacvinsky Daisak Bluni PLLC

(57) ABSTRACT

Acoustic energy is delivered to innervated vascular that contributes to renal sympathetic nerve activity, such as innervated tissue of the renal artery and abdominal aorta. Focused acoustic energy is delivered via an intravascular device of sufficient power to ablate innervated renal or aortal tissue. Focused acoustic energy may be delivered via an intravascular or extracorporeal device to image and locate target innervated renal or aortal tissue. Intravascular, extravascular, or transvascular focused ultrasound devices provide for high precision denervation of innervated vascular to terminate renal sympathetic nerve activity.

18 Claims, 22 Drawing Sheets

(51) Int. Cl.
*A61B 8/12* (2006.01)
*A61B 18/02* (2006.01)
*A61B 19/00* (2006.01)
*A61N 7/00* (2006.01)
*A61B 18/00* (2006.01)

(52) U.S. Cl.
CPC .... *A61B 2019/528* (2013.01); *A61N 2007/003* (2013.01); *A61N 2007/0095* (2013.01)

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Pflueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,609,606 A | 3/1997 | O'Boyle et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |

(56) References Cited

U.S. PATENT DOCUMENTS

| | | |
|---|---|---|
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,656 E | 11/1997 | Feinberg et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A | 2/1998 | Stern et al. |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy-Chutorian et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |

(56) References Cited

U.S. PATENT DOCUMENTS

| | | |
|---|---|---|
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |

(56) References Cited

U.S. PATENT DOCUMENTS

| | | |
|---|---|---|
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |

(56) References Cited

U.S. PATENT DOCUMENTS

| | | |
|---|---|---|
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |

(56) References Cited

U.S. PATENT DOCUMENTS

| | | |
|---|---|---|
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Christian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 * | 5/2010 | Carter et al. ............... 600/439 |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |

(56) References Cited

U.S. PATENT DOCUMENTS

| | | |
|---|---|---|
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,733 B2 | 12/2010 | Govari |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | Lafontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |
| 2001/0020126 A1 | 9/2001 | Swanson et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0049375 A1 | 4/2002 | Strommer et al. |
| 2002/0062146 A1 | 5/2002 | Makower et al. |
| 2002/0065542 A1 | 5/2002 | Lax et al. |
| 2002/0072710 A1 | 6/2002 | Stewart et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0028111 A1 | 2/2003 | Vaezy et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |

(56) References Cited

U.S. PATENT DOCUMENTS

| | | |
|---|---|---|
| 2003/0199747 A1 | 10/2003 | Michlitsch et al. |
| 2003/0225336 A1 | 12/2003 | Callister et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162550 A1 | 8/2004 | Govari et al. |
| 2004/0162555 A1 | 8/2004 | Farley et al. |
| 2004/0167506 A1 | 8/2004 | Chen |
| 2004/0176757 A1 | 9/2004 | Siheinikov et al. |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0243124 A1 | 12/2004 | Im et al. |
| 2004/0253304 A1 | 12/2004 | Gross et al. |
| 2004/0267132 A1* | 12/2004 | Podany .................. 600/459 |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0240116 A1* | 10/2005 | Saadat et al. .................. 600/549 |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0142801 A1 | 6/2006 | Demarais et al. |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0224153 A1 | 10/2006 | Fischell et al. |
| 2006/0229659 A1 | 10/2006 | Gifford et al. |
| 2006/0235474 A1 | 10/2006 | Demarais et al. |
| 2006/0239921 A1 | 10/2006 | Mangat et al. |
| 2006/0240070 A1 | 10/2006 | Cromack et al. |
| 2006/0241648 A1 | 10/2006 | Bleich et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0269555 A1 | 11/2006 | Salcedo et al. |
| 2006/0271111 A1 | 11/2006 | Demarais et al. |
| 2006/0276852 A1 | 12/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066957 A1 | 3/2007 | Demarais et al. |
| 2007/0066972 A1 | 3/2007 | Ormsby et al. |
| 2007/0073151 A1* | 3/2007 | Lee .............................. 600/439 |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0123851 A1 | 5/2007 | Alejandro et al. |
| 2007/0129633 A1 | 6/2007 | Lee et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0167821 A1* | 7/2007 | Lee et al. .................. 600/463 |
| 2007/0173805 A1 | 7/2007 | Weinberg et al. |
| 2007/0173899 A1 | 7/2007 | Levin et al. |
| 2007/0179496 A1 | 8/2007 | Swoyer et al. |
| 2007/0198007 A1 | 8/2007 | Govari et al. |
| 2007/0203480 A1 | 8/2007 | Mody et al. |
| 2007/0203549 A1 | 8/2007 | Demarais et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0213735 A1 | 9/2007 | Saadat et al. |
| 2007/0219576 A1 | 9/2007 | Cangialosi |
| 2007/0225781 A1 | 9/2007 | Saadat et al. |
| 2007/0232913 A1 | 10/2007 | Lau |
| 2007/0233170 A1 | 10/2007 | Gertner |

(56) References Cited

U.S. PATENT DOCUMENTS

| | | |
|---|---|---|
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1* | 2/2008 | Hissong et al. .................. 601/3 |
| 2008/0039830 A1 | 2/2008 | Munger et al. |
| 2008/0051454 A1 | 2/2008 | Wang |
| 2008/0058791 A1 | 3/2008 | Eberl |
| 2008/0064957 A1 | 3/2008 | Spence |
| 2008/0071269 A1 | 3/2008 | Hilario et al. |
| 2008/0071306 A1 | 3/2008 | Gertner |
| 2008/0082109 A1 | 4/2008 | Moll et al. |
| 2008/0086072 A1 | 4/2008 | Bonutti et al. |
| 2008/0086185 A1 | 4/2008 | Amurthur et al. |
| 2008/0091193 A1 | 4/2008 | Kauphusman et al. |
| 2008/0091251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0146918 A1 | 6/2008 | Magnin et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171944 A1 | 7/2008 | Brenneman et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0208182 A1 | 8/2008 | Lafontaine |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234780 A1 | 9/2008 | Smith |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0024195 A1 | 1/2009 | Rezai et al. |
| 2009/0030312 A1 | 1/2009 | Hadjicostis |
| 2009/0030411 A1 | 1/2009 | Werneth et al. |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112091 A1 | 4/2009 | Chiang |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204134 A1 | 8/2009 | Kassab |
| 2009/0204170 A1 | 8/2009 | Hastings et al. |
| 2009/0209885 A1 | 8/2009 | Babaev |
| 2009/0209949 A1 | 8/2009 | Ingle |
| 2009/0209951 A1 | 8/2009 | Marrouche |
| 2009/0210953 A1 | 8/2009 | Moyer et al. |
| 2009/0216317 A1 | 8/2009 | Cromack et al. |
| 2009/0221939 A1 | 9/2009 | Demarais et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0287202 A1 | 11/2009 | Ingle |
| 2009/0299355 A1 | 12/2009 | Bencini |
| 2009/0299356 A1 | 12/2009 | Watson |
| 2009/0306644 A1 | 12/2009 | Mayse et al. |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0057150 A1 | 3/2010 | Demarais et al. |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130815 A1* | 5/2010 | Gross et al. ..................... 600/30 |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0168777 A1 | 7/2010 | Stangenes et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |

(56) References Cited

U.S. PATENT DOCUMENTS

| | | |
|---|---|---|
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118598 A1 * | 5/2011 | Gertner ................. 600/431 |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0307034 A1 | 12/2011 | Hastings |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1180004 A1 | 2/2002 |
| EP | 1335677 B1 | 8/2003 |
| EP | 1579889 | 9/2005 |

(56) References Cited

FOREIGN PATENT DOCUMENTS

| | | |
|---|---|---|
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2204134 | 7/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2320821 B1 | 10/2012 |
| GB | 2456301 A | 7/2009 |
| WO | 9858588 A1 | 12/1998 |
| WO | 9900060 A1 | 1/1999 |
| WO | 0047118 A1 | 8/2000 |
| WO | WO0047118 | 8/2000 |
| WO | 03026525 A1 | 4/2003 |
| WO | 2004100813 A2 | 11/2004 |
| WO | 2004110258 A2 | 12/2004 |
| WO | WO2004110258 | 12/2004 |
| WO | WO2006022790 | 3/2006 |
| WO | WO2006041847 | 4/2006 |
| WO | WO2006041881 | 4/2006 |
| WO | 2006105121 A2 | 10/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |
| WO | 2008014465 A2 | 1/2008 |
| WO | WO2008003058 | 1/2008 |
| WO | WO2008061150 | 5/2008 |
| WO | WO2008061152 | 5/2008 |
| WO | WO2008070413 | 6/2008 |
| WO | 2009121017 A1 | 10/2009 |
| WO | 2010067360 A2 | 6/2010 |
| WO | WO2010067360 | 6/2010 |
| WO | WO2010078175 | 7/2010 |
| WO | 2010102310 A2 | 9/2010 |
| WO | WO2010129661 | 11/2010 |
| WO | 2011005901 A2 | 1/2011 |
| WO | 2011053757 A1 | 5/2011 |
| WO | 2011053772 A1 | 5/2011 |
| WO | WO2011053757 | 5/2011 |
| WO | WO2011053772 | 5/2011 |
| WO | 2011091069 A1 | 7/2011 |
| WO | WO2011091069 | 7/2011 |
| WO | 2011130534 A2 | 10/2011 |
| WO | WO2011130005 | 10/2011 |
| WO | WO2011139589 | 11/2011 |
| WO | 2012019156 A1 | 2/2012 |
| WO | WO2012019156 | 2/2012 |
| WO | 2013049601 A2 | 4/2013 |

OTHER PUBLICATIONS

Lafon et al., "Optimizing the Shape of Ultrasound Transducers for Interstital Thermal Ablation", Medical Physics, vol. 29, Issue 3, 2002, 8 pages.
Invitation to Pay Additional Search Fees dated Feb. 17, 2011 from PCT Application No. PCT/US2010/062458, 8 pages.
International Search Report and Written Opinion dated May 10, 2011 from PCT Application No. PCT/US2010/062457, 10 pages.
U.S. Appl. No. 12/980,952, filed Dec. 29, 2010, Rizq et al.
U.S. Appl. No. 12/980,972, filed Dec. 29, 2010, Vrba et al.
U.S. Appl. No. 61/324,163, filed Apr. 14, 2010, Hastings et al.
Toytman et al., "Tissue Dissection with Ultrafast Laser Using Extended and Multiple Foci", SPIE Proceedings, Optical Interactions with Tissues and Cells XXI, vol. 7562, 2010, 10 pages.
Blue Cross Blue Shield Medical Policy, "Surgery Section—MRI-Guided Focused Ultrasound (MRgFUS) for the Treatment of Uterine Fibroids and Other Tumors", 2004, 5 pages.
Seip et al., "Transurethral High Intensity Focused Ultrasound: Catheter Based Prototypes and Experimental Results", IEEE Ultrasonics Symposium Proceedings, 2000, 4 pages.
U.S. Appl. No. 13/225,962, filed Sep. 6, 2011, Hastings.
U.S. Appl. No. 13/227,446, filed Sep. 7, 2011, Hastings et al.
U.S. Appl. No. 13/243,114, filed Sep. 23, 2011, Jenson et al.
U.S. Appl. No. 13/243,134, filed Sep. 23, 2011, Sogard et al.
U.S. Appl. No. 13/283,203, filed Oct. 27, 2011, Hastings.
U.S. Appl. No. 13/295,182, filed Nov. 14, 2011, Hastings.
Lafon et al., "Optimizing the Shape of Ultrasound Transducers for Interstitial Thermal Ablation", Med Phys. Mar. 2002; 29(3): 290-7 (abstract only).
G. Ter Haar, "Ultrasound Focal Beam Surgery", Ultrasound in Med. & Biol., 1995, vol. 21, No. 9, pp. 1089-1100.
Zhou et al., "Non-Thermal Ablation of Rabbit Liver VX2 Tumor by Pulsed High Intensity Focused Ultrasound Contrast Agent: Pathological Characteristics", World Journal of Gastroenterology, vol. 14(43), Nov. 21, 2008, pp. 6743-6747.
Invitation to Pay Additional Fees dated Aug. 4, 2011 for PCT Application No. PCT/US2011/032524, 6 pages.
International Search Report and Written Opinion dated Oct. 26, 2011 for PCT Application No. PCT/US2011/032524, 16 pages.
Invitation to Pay Additional Fees dated Jan. 30, 2012 for PCT Application No. PCT/US2011/061157, 7 pages.
International Search Report and Written Opinion dated Dec. 23, 2011 for PCT Application No. PCT/US2011/050731, 14 pages.
Baun, "Interaction with Soft Tissue", Principles of General & Vascular Sonography, Chapter 2, pp. 23-34, Mar. 5, 2009.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.

(56) References Cited

OTHER PUBLICATIONS

Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
US 8,398,630, 03/2013, Demarais et al. (withdrawn)

* cited by examiner

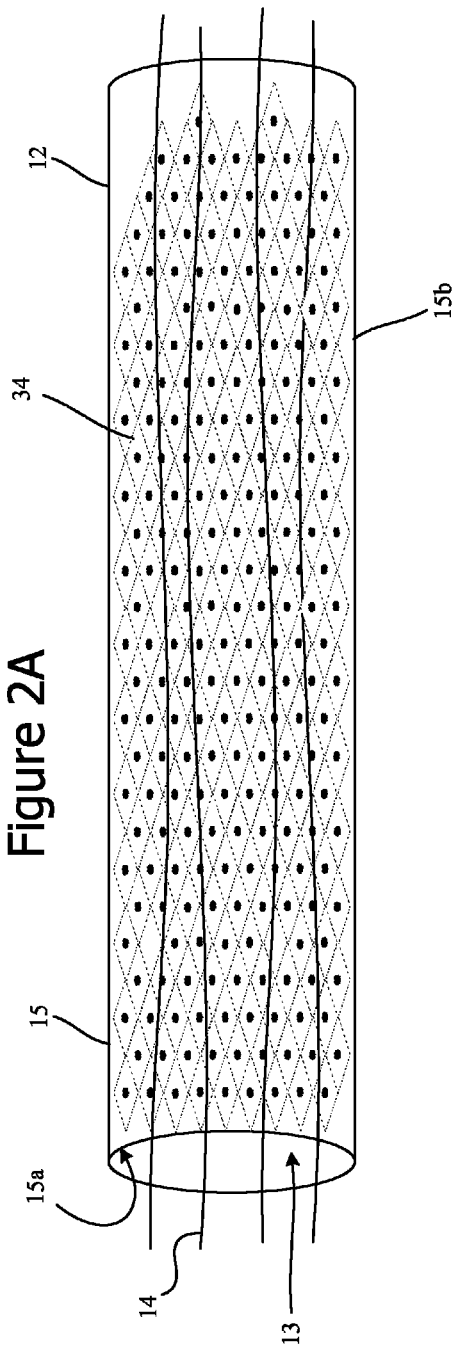
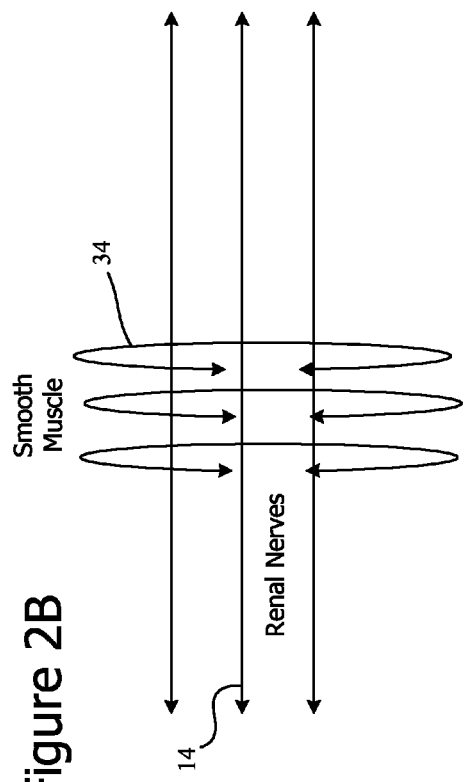
Figure 2A
Figure 2B

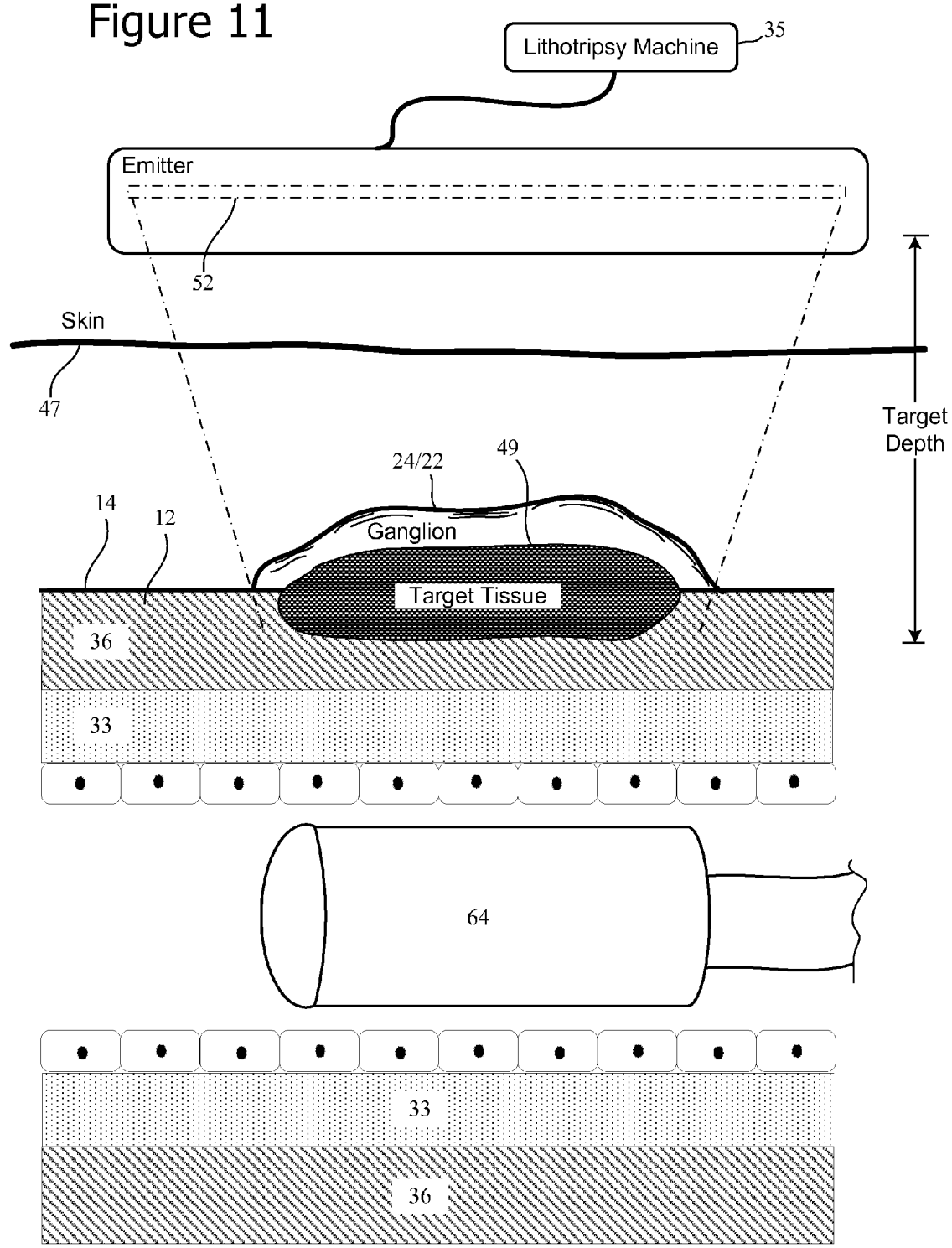

FOCUSED ULTRASONIC RENAL DENERVATION

RELATED APPLICATIONS

This application claims the benefit of Provisional Patent Application Ser. No. 61/324,164 filed on Apr. 14, 2010, to which priority is claimed pursuant to 35 U.S.C. §119(e) and which is hereby incorporated herein by reference in its entirety.

TECHNICAL FIELD

The present invention is related to systems and methods for denervating renal vasculature, including disruption and termination of renal sympathetic nerve activity, to improve cardiac and/or renal function.

BACKGROUND

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

SUMMARY

Devices, systems, and methods of the invention are directed to delivery of focused acoustic energy to innervated vasculature for one or both of imaging and ablating the innervated vasculature. Embodiments of the invention are directed to modifying renal sympathetic nerve activity using ultrasonic denervation therapy. Embodiments of the invention are directed to ultrasonic scanning or imaging of innervated tissues that contribute to renal sympathetic nerve activity.

In accordance with various embodiments, an apparatus includes a catheter configured for deployment within a vessel proximate innervated tissue that contributes to renal sympathetic nerve activity. An acoustic transducer is provided at a distal end of the catheter and dimensioned for deployment within the vessel proximate the innervated tissue. A focusing arrangement is positioned relative to the acoustic transducer and configured to focus acoustic energy outwardly beyond an inner wall of the vessel and into the innervated tissue at or proximate an outer wall of the vessel. A controller is configured to control the acoustic transducer for at least one of scanning tissue and ablating the innervated tissue. In some embodiments, the controller is configured to selectively control the acoustic transducer for scanning tissue and ablating innervated tissue.

In other embodiments, an apparatus includes a catheter configured for deployment within a vessel proximate innervated tissue, and an acoustic transducer is provided at a distal end of the catheter and dimensioned for deployment within the vessel. A focusing arrangement is positioned relative to the acoustic transducer and configured to focus acoustic energy outwardly beyond an inner wall of the vessel and into the innervated tissue at or proximate an outer wall of the vessel. A cryoballoon is dimensioned for deployment within the vessel and configured to freeze the innervated tissue. The acoustic transducer and focusing arrangement cooperate to deliver acoustic energy to frozen innervated tissue at an intensity sufficient to disrupt nerve cells of the innervated tissue.

According to some embodiments of the invention, an apparatus for facilitating delivery of acoustic energy to innervated vasculature includes a catheter configured for intravascular deployment and an ultrasound unit coupled to the catheter. An acoustic phased array transducer is provided at a distal end of the catheter and coupled to the ultrasound unit. The phased array transducer comprises a multiplicity of acoustic elements. Driver electronics are coupled to the phased array transducer. A controller is coupled to the driver electronics and configured to control activation of each of the acoustic elements of the phased array transducer for one or both of scanning and ablating target tissue of the innervated vasculature. The ultrasound unit may be an external unit or an internal unit. The ultrasound unit may be integrated at least in part at the distal end of the catheter, and the acoustic transducer may be integral or coupled to the ultrasound unit.

In other embodiments, an apparatus for facilitating delivery of acoustic energy to innervated vasculature includes a catheter configured for intravascular deployment and an ultrasound unit coupled to the catheter. An acoustic transducer is provided at a distal end of the catheter and coupled to the ultrasound unit. The acoustic transducer is configured for high intensity focused ultrasound operation in at least a cavitation ablation mode that forms bubbles within target tissue of the innervated vasculature and work to mechanically disrupt nerve fibers and ganglia included within the target tissue upon implosion or explosion.

In accordance with some embodiments, an apparatus for facilitating delivery of acoustic energy to innervated vasculature includes an imaging device configured for scanning the innervated vasculature and locating target tissue of the innervated vasculature. A catheter is configured for intravascular deployment and is coupled to an ultrasound unit. An acoustic transducer is provided at a distal end of the catheter and coupled to the ultrasound unit. The acoustic transducer is configured to deliver acoustic energy to the target tissue sufficient to ablate the target tissue located by the imaging device.

In further embodiments, an apparatus for facilitating delivery of acoustic energy to innervated vasculature includes a catheter configured for intravascular deployment and comprises an ultrasound unit coupled to the catheter. The apparatus includes an acoustic transducer provided at a distal end of the catheter and coupled to the ultrasound unit. The acoustic transducer is configured to deliver acoustic energy to target tissue of the innervated vasculature sufficient to ablate the target tissue. A balloon arrangement is configured to encompass at least the acoustic transducer. The balloon arrangement comprises a balloon that inflates under a very low pressure of about 1 to 2 pounds per square inch (PSI) or less above an ambient pressure that is adjacent to and outside the balloon.

According to other embodiments, an apparatus for facilitating delivery of acoustic energy to innervated vasculature includes a cryoballoon arrangement dimensioned for intravascular deployment and configured to freeze target tissue of the innervated vasculature. A catheter is configured for intravascular deployment and comprises an acoustic transducer at a distal end of the catheter. The acoustic transducer is coupled to an ultrasound unit. The acoustic transducer is configured to deliver acoustic energy to the frozen target tissue sufficient to destroy nerve cells of the target tissue.

In accordance with other embodiments, an apparatus for facilitating delivery of acoustic energy to innervated vasculature includes a cryoballoon arrangement dimensioned for intravascular deployment and configured to provide cooling for the innervated vasculature, such as the renal artery. A catheter is configured for intravascular deployment and comprises an acoustic transducer at a distal end of the catheter. The acoustic transducer is coupled to an ultrasound unit. The acoustic transducer is configured to deliver acoustic energy to the target tissue sufficient to destroy nerve cells of the target tissue.

In other embodiments, an apparatus of the invention facilitates delivery of acoustic energy to innervated vasculature that includes a ganglion that contributes to renal sympathetic nerve activity. The apparatus includes a catheter configured for intravascular deployment and is coupled to an ultrasound unit. The apparatus includes an acoustic focusing arrangement and an acoustic transducer provided at a distal end of the catheter, the acoustic transducer positioned relative to the focusing arrangement. The acoustic transducer and focusing arrangement are configured to deliver acoustic energy to a target ganglion of the innervated vasculature sufficient to destroy nerve cells included within the target ganglion.

In accordance with other embodiments, an apparatus for facilitating delivery of acoustic energy to innervated vasculature includes an imaging device configured for scanning the innervated vasculature and locating target tissue of the innervated vasculature. The apparatus includes a lithotripsy device configured to deliver high-energy acoustic shockwaves to the target tissue sufficient to denervate the target tissue located by the imaging device. A cryotherapy arrangement may be included, which is dimensioned for intravascular deployment and configured to freeze the target tissue. Nerve tissue, if damaged, has the potential to regenerate, especially if the nerve containing sheath has not been disrupted. New nerve growth occurs typically through the existing nerve sheath. If the nerve sheaths are disrupted or cut, nerve regenesis to the end organ is more difficult. An apparatus that combines both a freezing action followed by a mechanical acoustic wave action has the advantage of disrupting the nerve sheaths and preventing nerve regeneration to the targeted organ.

In further embodiments, an apparatus for facilitating delivery of an ablation agent to innervated vasculature includes an imaging device configured for scanning the innervated vasculature and locating a target ganglion of the renal artery or the abdominal aorta that contributes to renal sympathetic nerve activity. A delivery catheter is dimensioned for intravascular deployment in a vessel proximate the renal artery or the abdominal aorta. The delivery catheter includes a tissue penetrating feature configured to penetrate a wall of the vessel to create an access hole and to penetrate the target ganglion. A steering mechanism is configured for steering the delivery catheter through the access hole and to an extravascular location adjacent the target ganglion. A dispensing arrangement is configured to facilitate dispensing of an ablation agent from the delivery catheter into the target ganglion, whereby the ablation agent kills nerve cells of the target ganglion sufficient to terminate renal sympathetic nerve activity. The dispensing arrangement may be configured to facilitate dispensing of a neurotoxin, a venom, a cryogenic agent, a radioactive material, or radioactive seeds.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DESCRIPTION OF THE DRAWINGS

FIGS. 2A and 2B illustrate sympathetic innervation of the renal artery;

FIG. 11 illustrates a lithotripsy machine which is preferably operated in cooperation with a cryoballoon arrangement deployed in a renal artery in accordance with embodiments of the invention;

Figure 1:
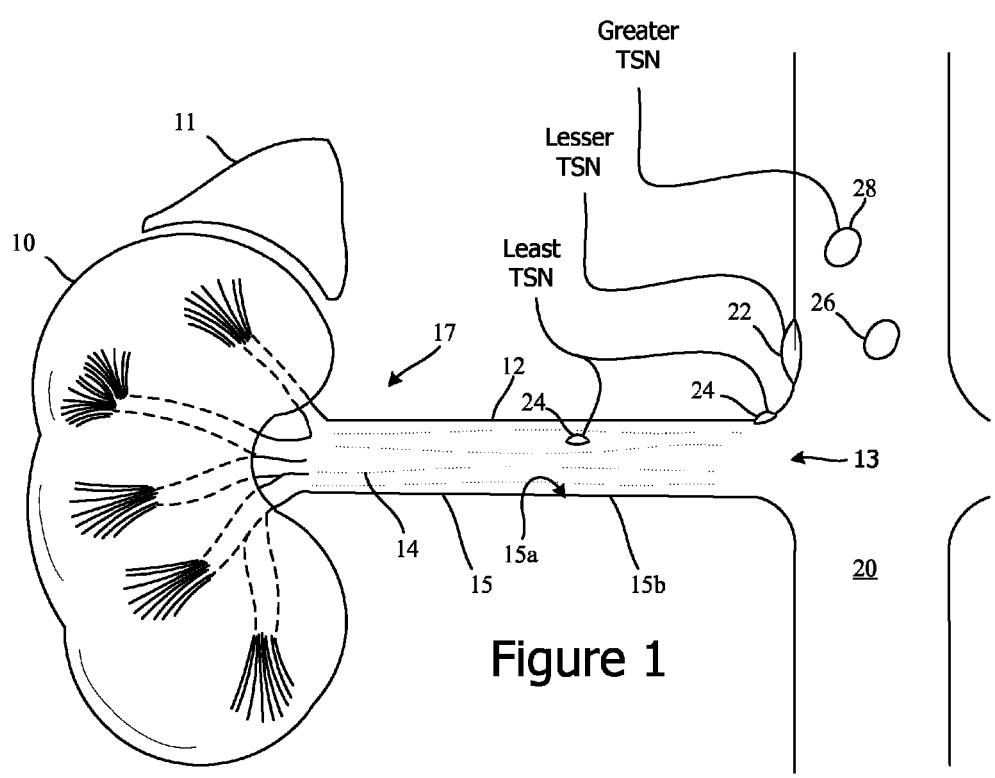
FIG. 1 is an illustration of a right kidney and renal vasculature including a renal artery branching laterally from the abdominal aorta.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION

In the following description, references are made to the accompanying drawings which illustrate various embodiments of the invention. It is to be understood that other embodiments may be utilized, and structural and functional changes may be made to these embodiments without departing from the scope of the present invention.

Embodiments of the invention are directed to systems, devices, and procedures for delivering ultrasonic denervation therapy to innervated renal vasculature. Embodiments of the invention are directed to systems, devices, and procedures for denervating renal vasculature using ultrasonic denervation therapy to disrupt target tissue so that renal sympathetic nerve activity is permanently terminated. Embodiments of the invention are directed to systems, devices, and procedures for scanning or imaging innervated renal vasculature to locate target tissue for denervation and to evaluate the efficacy of ultrasonic denervation therapy delivered to the target tissue. Other approaches may be used to evaluate the effectiveness of an ultrasonic denervation treatment, such as an electrode arrangement (e.g., electrode array) arranged at spaced-apart locations relative to innervated target tissue, which can sense nerve activity along nerve fibers (and at ganglia) of the innervated target tissue.

The disclosed embodiments are generally directed to imaging and/or denervating innervated renal vascular tissue that contributes to renal function, particularly renal sympathetic nerve activity. Target innervated vasculature of the renal artery, for example, preferably includes renal nerves, renal ganglia, aortal ganglia and other nerves and ganglia that contribute to renal sympathetic nerve activity. Although preferred embodiments of the invention provide for complete and permanent termination of renal sympathetic nerve activity, various embodiments may be implemented to provide for temporary (e.g., weeks or months) cessation of renal sympathetic nerve activity.

Representative embodiments of the invention described herein are generally directed to ultrasonic imaging and denervation apparatuses and therapies involving continuous or pulsed ultrasound at frequencies well above the human audible range of hearing, which corresponds to sound in the range of about 20 hertz to 20 kHz. The term "ultrasound" is intended to apply to all acoustic energy (e.g., longitudinal or transverse, mechanical waves) with a frequency greater than 20 kHz. Ultrasonic apparatuses according to embodiments of the invention typically operate at frequencies between about 1 MHz to about 80 MHz, with many apparatuses operating at frequencies between about 2 MHz to about 5 MHz. Intravascular and intracardiac ultrasonic imaging devices generally operate in the frequency range between about 5 MHz and 60 MHz.

According to various embodiments, ultrasonic apparatuses and procedures of the invention are directed to imaging renal tissue and/or positioning an ultrasonic denervation device within the renal artery or vein, for example. Various embodiments include an intravascular (e.g., endovascular, intra-to-extra vascular, or transvascular) ultrasonic denervation device configured to provide both imaging of, and denervation therapy to, target tissue of innervated renal vasculature.

Other embodiments include an intravascular ultrasonic denervation device configured to provide denervation therapy to target tissue of innervated renal vasculature, with imaging provided by a separate device, which may be an endovascular, intra-to-extravascular, transvascular, extravascular, or extracorporeal imaging device or system.

In general, suitable scanning, imaging and/or locating apparatuses provide target depth, range, and or volume data that are used by the system computer to facilitate locating of target tissue and adjustment of various device or system parameters, such as power parameters (e.g., amplitude, frequency, continuous mode, pulse mode, etc.), focus parameters (e.g., focal length, beam spread and/or divergence, phased array pulse duration and sequencing, etc.), and operating mode (e.g., scan, denervate, and concurrent scan+denervate modes), among others.

Data associated with imaging and denervation procedures may be communicated to an external system which produces imaging data and visual information useful for positioning the ultrasonic denervation device and evaluating the efficacy of an ultrasonic denervation procedure. The external system, for example, may include a computer which includes a display. Data and visual information concerning the scanning and ultrasonic denervation therapy procedures are preferably presented on the display. The computer may include an interface for communicating with other systems and devices, including a network or server.

Various embodiments of the invention are directed to apparatuses that deliver focused acoustic energy to target tissue that causes an increase in the temperature of the target tissue to a level that disrupts nerve structures of the target tissue and prevents chronic recovery of nerve fibers/ganglion in the target tissue resulting from the burn injury. Other embodiments are directed to apparatuses that deliver focused energy to target tissue that causes mechanical disruption of target tissue and prevents chronic recovery of nerve fibers/ganglion in the target tissue resulting from the mechanical disruption (e.g., cavitation microbubbles). Preferred ultrasound apparatuses include those that achieve a desired level of disruption of target tissue while leaving adjacent or intervening tissue uninjured or negligibly injured (e.g., subject to healing without permanent adverse effects).

The frequency of acoustic energy generated by ultrasonic apparatuses of the invention is preferably selected so that acoustic energy is absorbed substantially in the wall of the renal artery, preferably the outer wall region. In some embodiments, the ultrasonic apparatus is configured to emit acoustic energy of sufficient power to raise the temperature of targeted renal artery wall tissue to above 50° C. to kill the target artery tissue and nerve/ganglion within it. In other embodiments, the ultrasonic apparatus is configured to emit acoustic energy of sufficient power to raise the temperature of targeted renal artery wall tissue to above 65° C. to reform the collagen in target artery wall tissue and mechanically change the tissue property. In further embodiments, the ultrasonic apparatus is configured to emit acoustic energy of sufficient power to raise the temperature of targeted renal artery wall tissue to between 65° C. and 100° C. to render the fat from the target tissue, and totally disrupt the target tissue and prevent chronic recovery of the nerve fibers/ganglion from the burn injury.

Embodiments of the invention are directed to an intravascular device that includes a focused ultrasonic transducer, such as a High Intensity Focused Ultrasound (HIFU) device. HIFU is a highly accurate medical technology that uses high-intensity focused ultrasound to heat and destroy target tissue rapidly. A HIFU approach can focus acoustic energy to generate heat deep within target tissue at a substantial distance from the ultrasonic transducer. An important difference between HIFU and other forms of focused energy, such as RF or radiation therapy, is that the passage of ultrasound energy through intervening tissue has no apparent cumulative effect on the intervening tissue.

According to various embodiments, a HIFU transducer is incorporated or otherwise supported by a catheter dimensioned for deployment in the renal artery, renal vein, abdominal aorta, or other vessel near the kidneys. The HIFU transducer generates ultrasound beams that can be focused on target tissue located near to, or relatively distant from, the transducer. For example, embodiments of an intravascular HIFU transducer of the present invention may be used to inject acoustic energy into target tissue located about 0.5 mm to about 90 mm away from the HIFU transducer.

In short range applications, such as renal artery denervation conducted from within the renal artery, an intravascular HIFU device may be used to inject acoustic energy into target tissue of the renal artery located about 1 mm to about 4 mm away from the HIFU transducer. In long range applications, such as renal artery denervation conducted from within the renal vein or abdominal aorta, an intravascular HIFU device may be used to inject acoustic energy into target tissue of the renal artery located about 5 mm to about 80 mm away from the HIFU transducer.

Using a HIFU transducer of the present invention, one or more focal zones at or within a location, region, or volume within target tissue can be subjected to high intensity ultrasound energy, while tissue surrounding the target tissue is subjected to much lower intensity ultrasound energy. In this manner, target tissue can be heated to a sufficiently high temperature so as to cause a desired thermal effect (e.g., ablation, coagulation, denaturation, necrosis) while tissue surrounding the target area is not subject to damaging temperatures. Due to the significant energy deposition at the focal zone, the temperature within the target tissue rises to 65° to 85° C., destroying the target tissue, which includes nerves and/or ganglia, by coagulative necrosis.

Each sonication of the ultrasonic beams emitted by the HIFU transducer treats a precisely defined portion of the target tissue. HIFU denervation may be accomplished manually, automatically, or semi-automatically. For example, renal artery denervation may be accomplished by moving an intravascular HIFU transducer arrangement within the renal artery by robotic control of the catheter to which the HIFU transducer is connected. By way of further example, renal artery denervation may be accomplished by moving (translating and/or rotating) an intravascular HIFU transducer arrangement relative to a catheter to which the HIFU transducer is connected via electronic motor control.

Ultrasonic denervation therapy using acoustic energy involves the conversion of acoustic energy into heat when acoustic energy is absorbed by target tissue. Illumination of target tissue that includes nerves and ganglia with acoustic energy, for example, leads to thermal damage of the target tissue. The diffusion of heat energy into the surrounding tissue, however, can thermally damage tissue outside the target area or volume of tissue. A cooling apparatus is preferably used to minimize thermal trauma to the surrounding tissue. Various cooling apparatuses are contemplated herein for this purpose, including cryoballoons, cryocatheters, irrigation arrangements, cooling lumens, Peltier cooling apparatuses, and blood diversion apparatuses, among others.

In embodiments that utilize focused ultrasound, such as HIFU, local cooling apparatuses may not be required or desired, because focused acoustic energy can be projected to target tissue spaced apart from the ultrasonic transducer (e.g., by 1-90 mm) without heating tissue surrounding the target tissue.

Turning now to the figures, FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the present invention. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

The kidneys and ureters (not shown) are innervated by the renal nerves 14. FIGS. 1 and 2A-2B illustrate sympathetic innervation of the renal vasculature, primarily innervation of the renal artery 12 and distal structures such as the kidney 10. The primary functions of sympathetic innervation of the renal vasculature include regulation of renal blood flow, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Dilation and contraction of the distal bed of renal arterioles fed by the renal artery is similarly controlled by distal branches of the renal autonomic nerves, and these "resistance vessels" are most important in determining the total blood flow through the renal artery. Conversely, increased parasympathetic activity tends to relax the smooth muscle 34, while decreased parasympathetic activity tends to cause smooth muscle contraction.

Figure 3A:
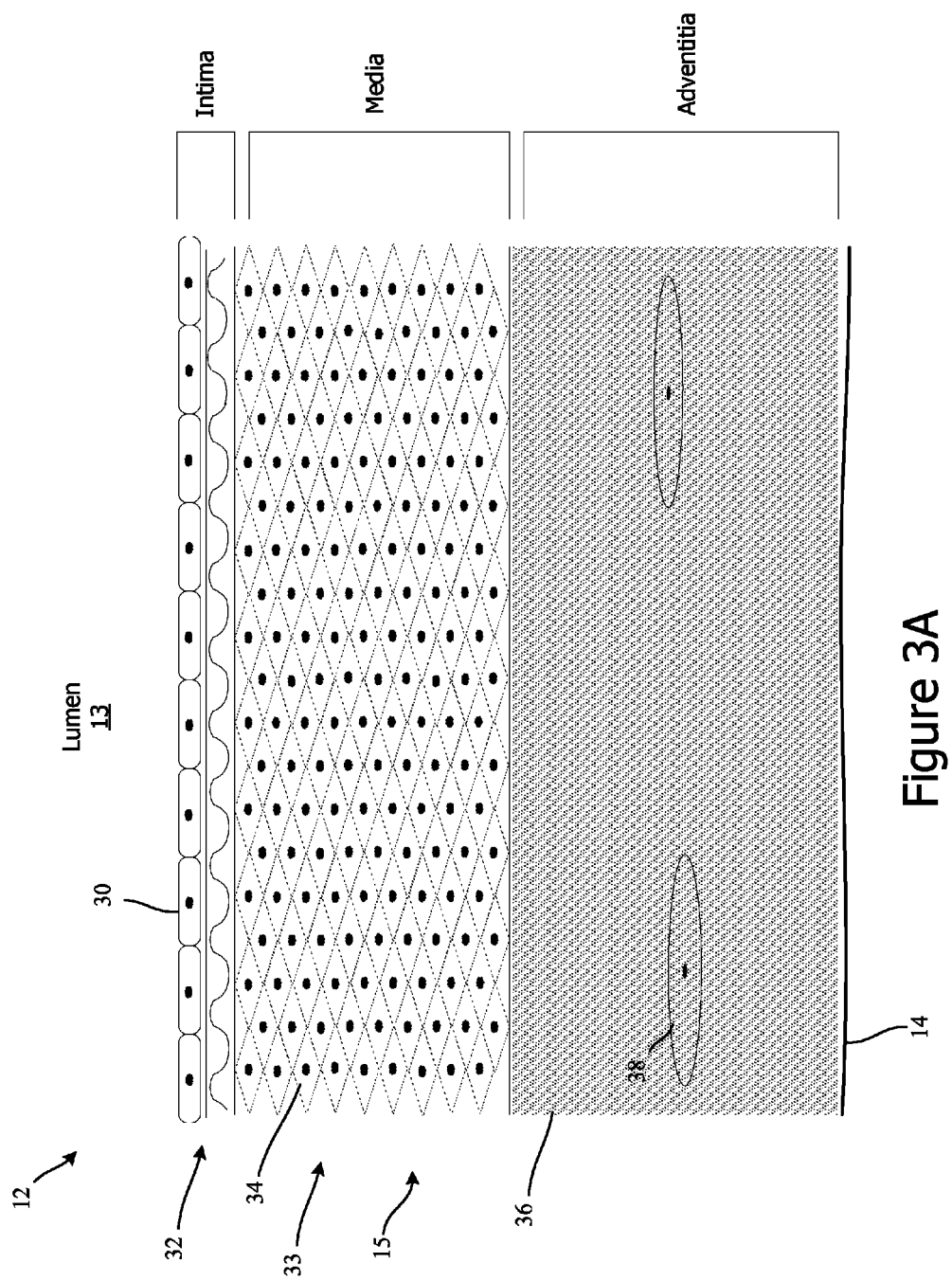
FIG. 3A illustrates various tissue layers of the wall of the renal artery.
Figure 3B:
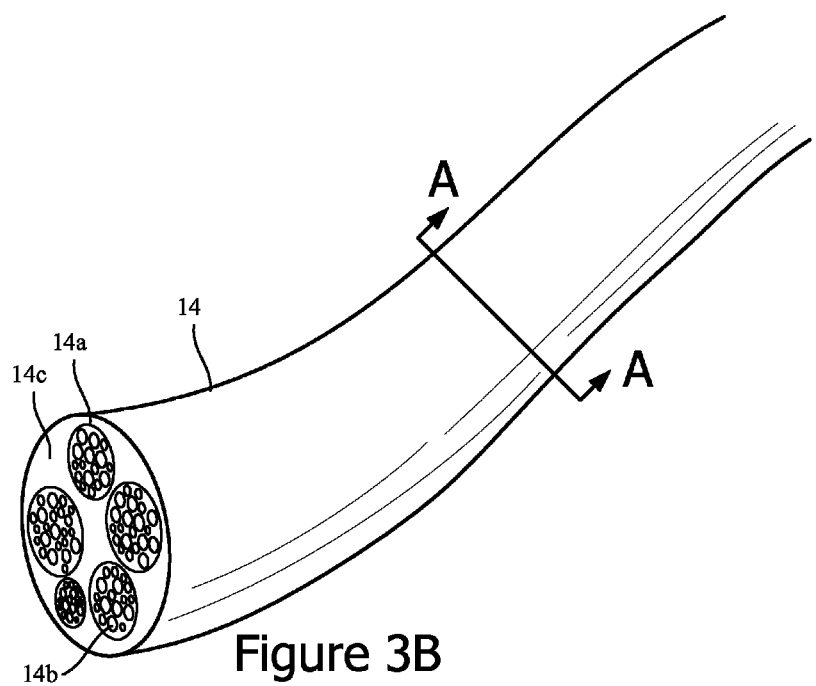
FIGS. 3B and 3C illustrate a portion of a renal nerve.
Figure 3C:
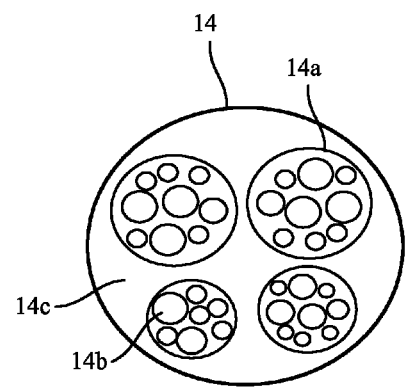

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A renal nerve 14 is shown proximate the adventitia 36 and extending longitudinally along the renal artery 12. The main trunk of the renal nerves 14 generally lies at or adjacent the adventitia of the renal artery 12, with certain branches coursing into the media to enervate the renal artery smooth muscle. For example, renal nerves may be situated in the adventitia proximate the outer wall of the renal artery (e.g., tunica adventitia) or within the vasa vasorum, such as the vasa vasorum externae.

Figure 4:
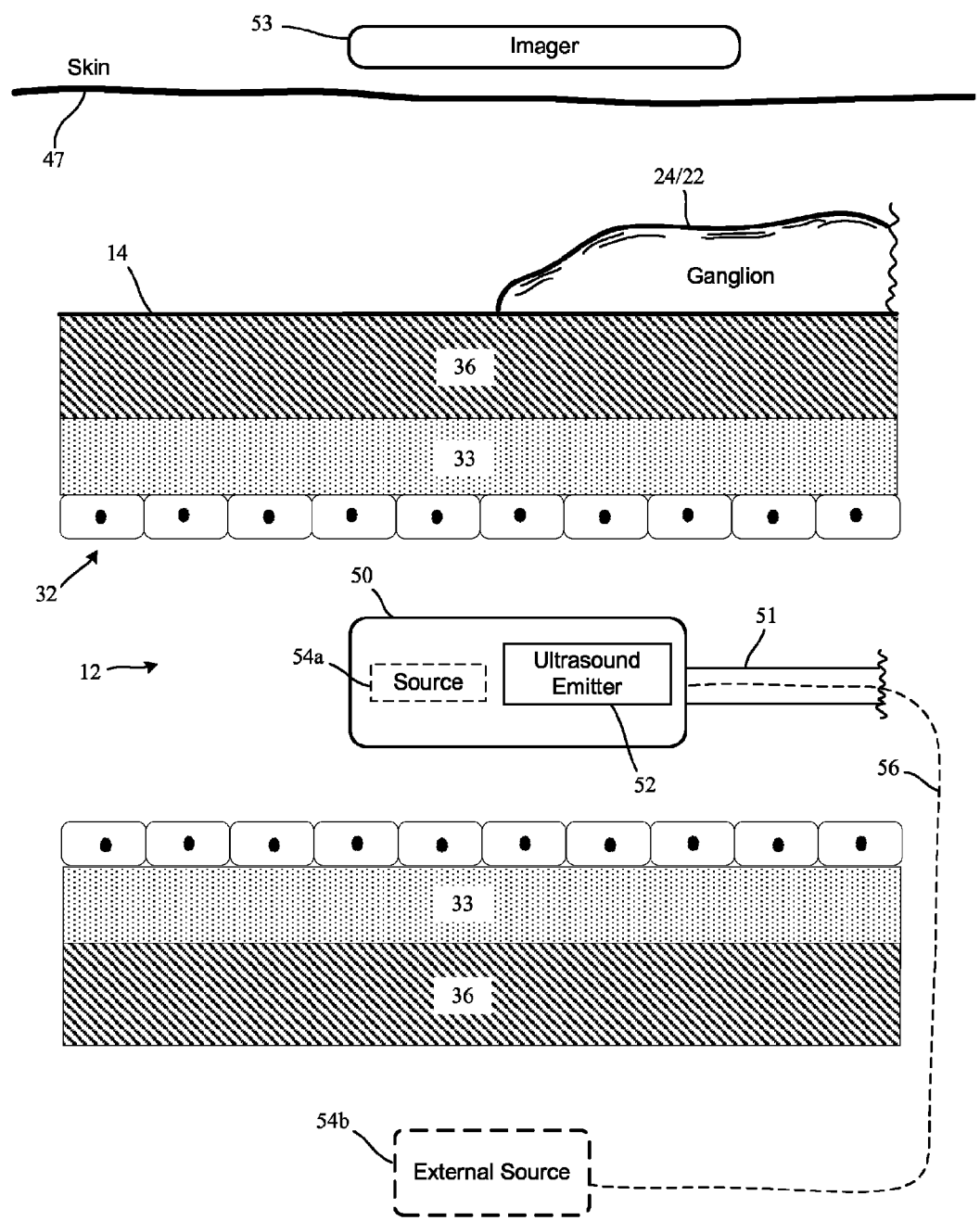
FIG. 4 illustrates an ultrasound unit deployed in a renal artery and an optional external imaging system or device in accordance with embodiments of the invention.
Figure 5:
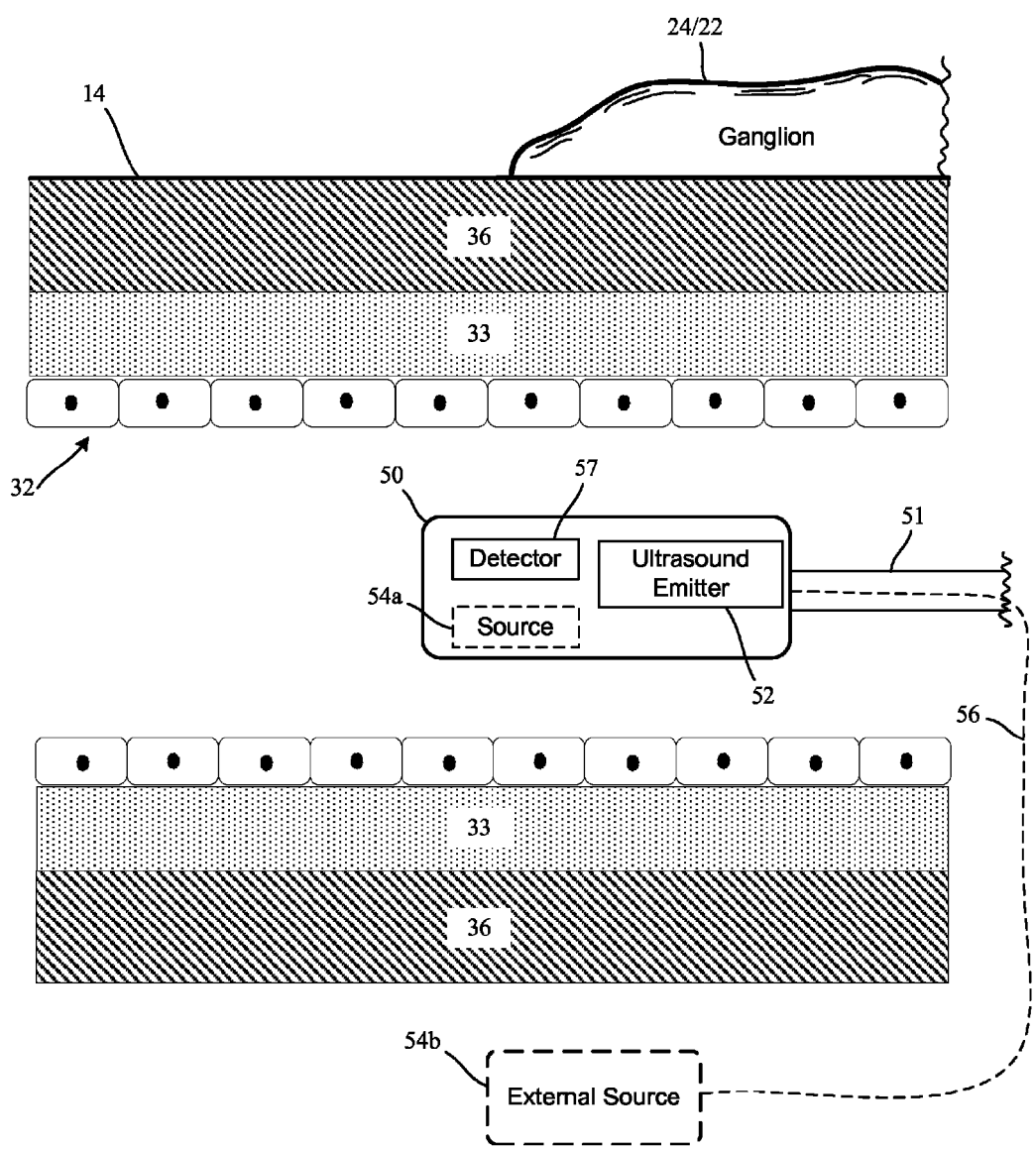
FIG. 5 illustrates an ultrasound unit deployed in a renal artery which incorporates one or both of imaging and ultrasonic denervation therapy delivery capabilities in accordance with embodiments of the invention.
Figure 6:
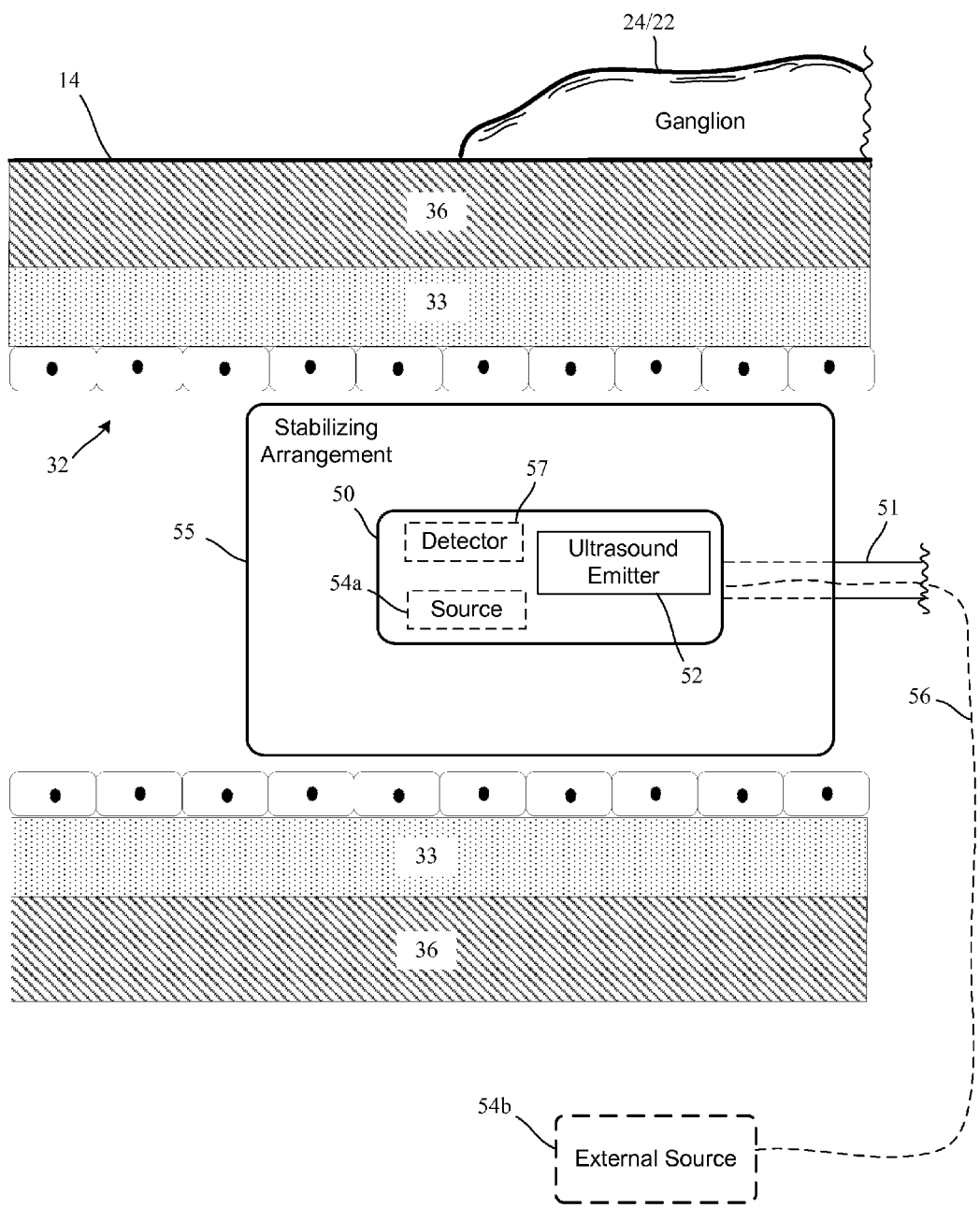
FIG. 6 illustrates an ultrasound unit deployed in a renal artery using a stabilization arrangement in accordance with embodiments of the invention.

FIGS. 4-6 illustrate ultrasound arrangements for treating innervated renal and/or aortic tissue that contribute to renal sympathetic nerve activity in accordance with embodiments of the invention. FIGS. 4-6 show an exaggerated sectional view of a portion of a patient's renal artery 12. The tissue layers of the renal artery 12 include the intima 32, which comprises the endothelium, the media 33, which includes smooth muscle, and the adventitia 36. A renal nerve 14 and a ganglion (e.g., renal ganglion 24 or aorticorenal ganglion 22) are shown on or proximate an outer section of the adventitia 36 for illustrative purposes.

In various embodiments according to FIGS. 4-6, an ultrasound unit 50 comprises an ultrasound delivery apparatus capable of transmitting acoustic energy into innervated renal vasculature that disrupts target tissue which includes one or both of renal nerves 14 and ganglia 24/22. Acoustic energy transmitted by an emitter 52 of the ultrasound unit 50 is preferably sufficient to disrupt the target tissue so that renal sympathetic nerve activity is permanently terminated.

It is understood that in the embodiments shown in FIGS. 4-6 and in other figures, the ultrasound unit 50 may comprises components that are entirely or partially implantable, and may comprise components that are entirely or partially external of the patient. For example, the ultrasound unit 50 may comprise an implantable transducer and an external ultrasound source. By way of further example, the ultrasound unit 50 may comprise an implantable transducer and an implantable ultrasound source. An implantable ultrasound source may be powered by an implantable or external power source. In another example, the ultrasound unit 50 may be integrated at least in part at the distal end of the catheter, and the acoustic transducer may be integral or coupled to the ultrasound unit. Other configurations are contemplated herein.

In other embodiments, an ultrasound unit 50 comprises an ultrasound delivery apparatus capable of transmitting acoustic energy into innervated renal vasculature that facilitates locating of renal nerves 14 and ganglia 24/22 but insufficient to significantly disrupt renal sympathetic nerve activity (e.g., insufficient to effect appreciable or permanent cessation of renal sympathetic nerve activity). In such embodiments, the ultrasound unit 50 may be used in combination with a detector to facilitate imaging and locating of target structures within or near renal artery and aortic tissue.

In further embodiments, an ultrasound unit 50 comprises an ultrasound delivery apparatus capable of transmitting acoustic energy into innervated renal vasculature that facilitates locating of renal nerves 14 and ganglia 24/22 within target tissue and transmitting acoustic energy into the target tissue that significantly disrupts renal sympathetic nerve activity, such as by permanently terminating renal sympathetic nerve activity. In other embodiments, a separate internal or external imaging device may be used to facilitate locating of renal nerves 14 and ganglia 24/22 within target tissue, and an intravascular ultrasound unit 50 is configured to transmit acoustic energy into the target tissue sufficient to significantly or permanently disrupt renal sympathetic nerve activity.

According to the embodiments shown in FIGS. 4-6, an ultrasound unit 50 includes an ultrasonic emitter 52 disposed in a housing to which a distal end of a catheter 51 is connected. The emitter 52 is coupled to an ultrasonic source 54. The emitter 52 typically includes, or is adjacent to, an arrangement that facilitates focusing of acoustic energy received from the ultrasonic source 54 and directs acoustic energy to target renal tissue. In some embodiments, as shown in FIG. 4, the ultrasound unit 50 includes an ultrasonic emitter 52 and a separate imaging system 53 or device for imaging renal tissue and guiding acoustic energy emitted by the ultrasound unit 50 to the target renal tissue. The imaging system or device 53 may be used to assist in delivering and positioning the ultrasound unit 50 to and within the renal artery 12.

The imaging system or device 53 may be external to the patient (i.e., outside the skin 47) or at least partially implantable, such as an endovascular imaging device (e.g., IVUS or intravascular ultrasound device). Suitable intravascular, transvascular, extravascular, and extracorporeal apparatuses include various MRI, laser, and ultrasound apparatuses, for example.

In other embodiments, as shown in FIG. 5, the ultrasound unit 50 includes an ultrasonic emitter 52 and a detector 57 or other local imaging device for imaging renal tissue and directing acoustic energy to target tissue of the renal vasculature. The ultrasonic emitter 52 and detector 57 may be used to assist in delivering and positioning the ultrasound unit 50 to and within the renal artery 12. For example, the detector 57 may comprise an ultrasound detector that receives acoustic energy (e.g., echoes) reflected from the target tissue.

In various embodiments, a single transducer operates as the emitter 52 and the detector 57. In other embodiments, one transducer operates as the emitter 52 and another transducer operates as the detector 57. In further embodiments, the transducer that is configured to deliver denervation therapy is also operative as a scanning transducer. In some embodiments, separate denervation and scanning transducers are employed. It is understood that the emitter and/or receiver components shown in the figures may define single transducer elements or an array of transducer elements.

In some embodiments, for example, the ultrasound unit 50 is configured to selectively operate in a scan mode and a denervation mode, allowing the ultrasound unit 50 to locate target tissue in the scan mode and then permanently disrupt renal nerve fibers and ganglia within the target tissue in the denervation mode. Details of components and functionality that can be adapted for use in or by the ultrasound unit 50 are described in greater detail hereinbelow and disclosed in U.S. Pat. Nos. 5,344,395 and 5,601,526, which are incorporated herein by reference.

FIG. 6 shows another embodiment of an ultrasound arrangement for denervating renal vasculature that contributes to renal sympathetic nerve activity in accordance with the invention. A support or stabilizing arrangement 55 is provided to aid in maintaining the ultrasound unit 50 at a relatively constant distance from the artery wall as the ultrasound unit 50 is translated and/or rotated within the lumen of the renal artery 12.

In various configurations, it is desirable to stabilize the position of the ultrasound unit 50 within the renal artery 12 so that the intensity of the acoustic energy emitted by the ultrasound unit 50 does not vary significantly with location, which could otherwise result in over-treated and under-treated regions. One approach to keeping the ultrasound unit 50 at a constant distance from the wall of the renal artery is to incorporate the ultrasound unit 50 into a balloon which can be expanded until it fills the arterial lumen, embodiments of which are discussed below with reference to FIGS. 8-11. Other stabilizing arrangements 55 are contemplated, such as a stent or an expandable cage or basket arrangement.

In FIGS. 4-6, the emitter 52 may be coupled to an external ultrasonic source 54b via a coupling 56. The external ultrasonic source 54b is situated external to the renal artery, such as at a location outside the body. The coupling 56 is typically an electrical coupling disposed within a catheter, which enters the renal vasculature at a suitable access vessel location (e.g., superior or inferior abdominal aorta or inferior vena cava). In other embodiments, the ultrasonic source 54a can be disposed within the housing of the ultrasound unit 50 and may draw power from a power source internal to the ultrasound unit 50 (battery, capacitor, energy harvesting device) or from a patient-external power source. The ultrasonic source 54a may also be housed in a separate unit inside the body (e.g., a subcutaneous pocket or within the abdominal cavity, among other locations) and draw power from an internal power source or an external power source (e.g., via electromagnetic induction using an RF source external of the patient).

Locating target tissue may involve locating renal or aortic ganglia and/or artery tissue which includes renal nerves 14, such as the adventitia proximate the outer wall of the renal artery or the vasa vasorum externae. For example, one or more locating components of the ultrasound unit 50 may be used to scan the renal artery 12 or adjacent tissue that includes renal nerves and/or renal/aortal ganglia. The ultrasound unit 50 (or other locating apparatus, internal or external) may be controlled to scan for target tissue in deep layers of the adventitia and/or the vasa vasorum, such as the vasa vasorum externae which penetrates the outer adventitia (tunica adventitia). Once located, the target tissue may be treated using the ultrasound unit 50.

According to various embodiments that employ an external imager 53, such as that shown in FIG. 4, an MRI system may be used to locate target tissue (e.g., renal nerves and ganglia of the renal artery, vasa vasorum, and abdominal aorta), determine the depth, length, and/or width of the target tissue (e.g., for 1-D, 2-D, or 3-D imaging), and guide acoustic energy emitted by the ultrasound unit 50 to the target tissue. The MRI system may be used to identify renal nerves and ganglia of the renal artery, vasa vasorum, and abdominal aorta, before they are destroyed by the ultrasonic emitter 52. In accordance with embodiments that use high intensity focused ultrasound, Magnetic Resonance-guided Focused Ultrasound (MRg-FUS) apparatuses and techniques may be used to treat innervated target tissue.

An MRI system of the invention may be used to accurately quantify the heating of target tissue produced by the ultrasonic emitter 52 during a renal denervation procedure. For example, the MRI system preferably identifies the ultrasound path and monitors heat rise in the target tissue. An MRI system of the invention preferably provides for high soft tissue contrast and imaging in any orientation, which enhances guiding of HIFU ablation energy to target innervated renal vasculature.

Heating, position, and other imaging information developed by the MRI system is preferably used to aid in controlling ultrasonic ablation of target tissue, particularly when using a HIFU implementation. This information may be used to provide automatic (e.g., robotic) or semi-automatic (e.g., partially robotic) control of a renal denervation procedure in real-time (or near real-time), via the MRI system computer and/or physician, respectively.

In various embodiments, a real-time interactive MRI (rt-MRI) system is used to provide for concurrent imaging of target innervated renal vasculature by the MRI system and ablation of the target vasculature by the ultrasound unit 50. Embodiments of an interactive real-time MRI system include a highly parallel MRI device having upwards to 32 channels or more. For example, an MRI system of the invention may include 32-element phased arrays, which may be defined by multiple synchronized scanner-receiver subsystems. Software of the MRI system coordinates the real-time acquisition, reconstruction, and display of 32-channel images across the multiple subsystems.

Real-time, large field-of-view (FOV) imaging can be achieved by using interleaved echo-planar and single-shot fast-spin-echo pulse sequences. In one approach, parallel image acquisition is augmented by independently offsetting the frequency of different array elements to variably shift their FOV. When augmented parallel imaging is combined with conventional parallel imaging techniques, a significant increase of image acceleration factors can be achieved. Increasing the number of coils can significantly increase the FOV in two dimensions during rapid imaging, with no or negligible degradation of imaging time or spatial resolution.

Interactive real-time MRI in combination with an ultrasound unit 50 can enhance procedural safety by identifying unexpected complications early in a denervation procedure. A real-time MRI system of the invention preferably provides high tissue contrast in any orientation, which facilitates accurate locating of target tissue of the renal artery, vasa vasorum, and abdominal aorta. For example, a multi-slice, real-time MRI system may be used to guide ultrasound unit emissions across vascular tissue boundaries with high precision.

In other embodiments, an ultrasonographic imaging system 53 is used to locate target tissue, determine the depth, length, and/or width of the target tissue (e.g., for 1-D, 2-D, or 3-D imaging), and guide acoustic energy emitted by the ultrasound unit 50 to the target tissue within the renal artery 12, vasa vasorum, and abdominal aorta. In various embodiments that use high intensity focused ultrasound, Ultrasound-guided Focused Ultrasound (USgFUS) apparatuses and techniques may be used to treat innervated tissue of the renal artery. Suitable ultrasonographic systems include those configured with extracorporeal, intravascular, or transvascular imaging components.

In other embodiments, a combination of an ultrasonic device and a laser device is used to cooperatively provide imaging of, and denervation therapy to, innervated renal vasculature. According to some embodiments, one of the ultrasonic device and the laser device is used for imaging, while the other of the ultrasonic device and the laser device is used for renal denervation. The ultrasonic device or the laser device (or both, if desired) is capable of transmitting acoustic and/or optical energy into the renal artery wall sufficient to disrupt target tissue that includes renal nerves 14 and/or ganglia 24/22. The acoustic and/or optical energy is preferably sufficient to disrupt the target tissue so that renal sympathetic nerve activity is permanently terminated. Combinations of ultrasonic and laser devices that can be used cooperatively to image and denervate renal vasculature include ultrasonic and laser device combinations disclosed in previously cited commonly owned U.S. Patent Publication No. 2011/0257641, filed as U.S. Provisional Patent Application Ser. No. 61/324,163 on Apr. 14, 2010 and entitled "Phototherapy for Renal Denervation."

In other embodiments, a combination of an ultrasonic device and a laser device is used to cooperatively provide imaging of, and denervation therapy to, innervated renal vasculature. According to some embodiments, one of the ultrasonic device and the laser device is used for imaging, while the other of the ultrasonic device and the laser device is used for renal denervation. The ultrasonic device or the laser device (or both, if desired) is capable of transmitting acoustic and/or optical energy into the renal artery wall sufficient to disrupt target tissue that includes renal nerves 14 and/or ganglia 24/22. The acoustic and/or optical energy is preferably sufficient to disrupt the target tissue so that renal sympathetic nerve activity is permanently terminated. Combinations of ultrasonic and laser devices that can be used cooperatively to image and denervate renal vasculature include ultrasonic and laser device combinations disclosed in previously cited commonly owned U.S. Patent Publication No. 2011/0257641, filed as U.S. Provisional Patent Application Ser. No. 61/324,163 on Apr. 14, 2010 and entitled "Phototherapy for Renal Denervation."

Figure 7:
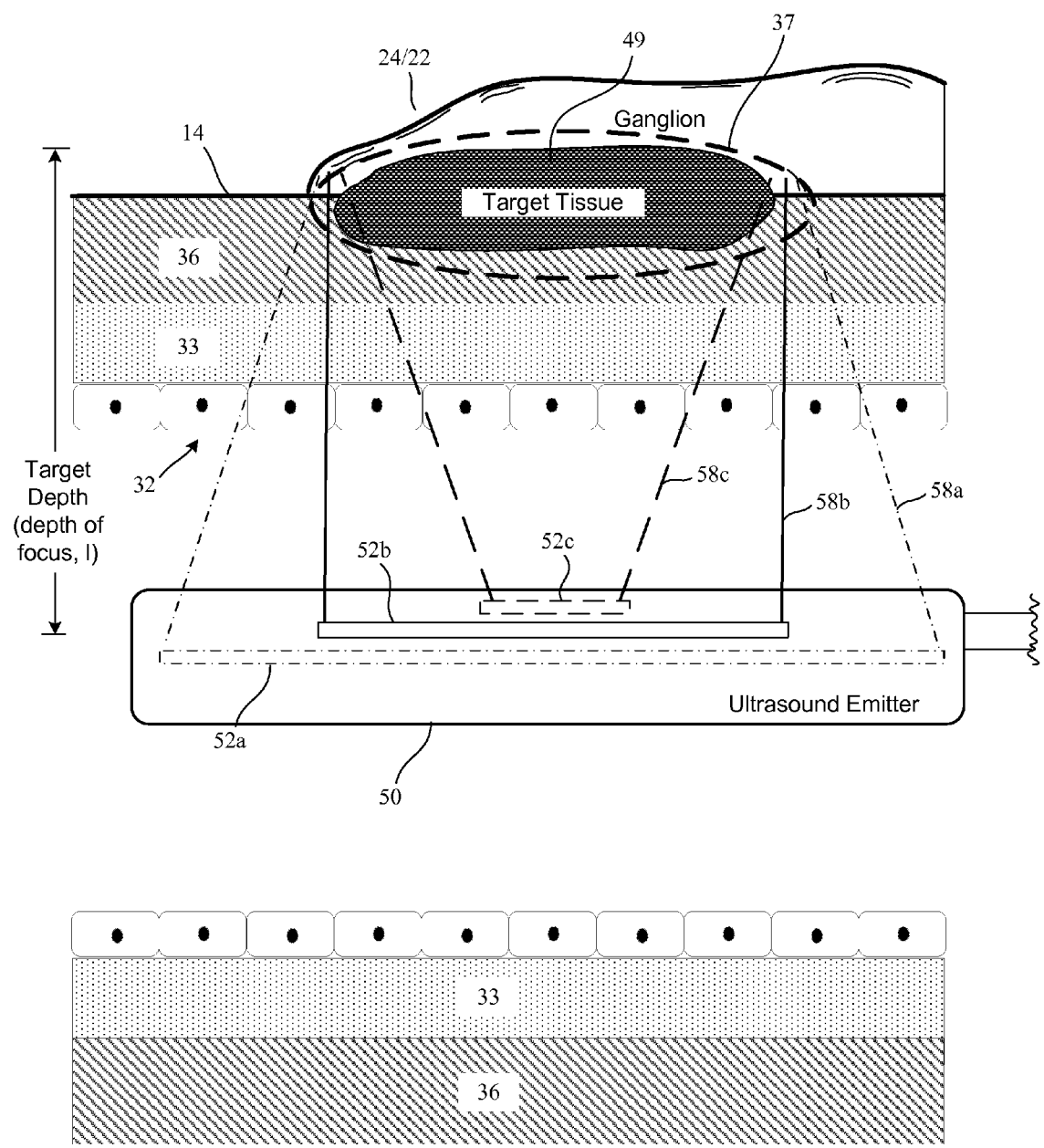
FIG. 7 shows different possible beam profiles of acoustic energy emitted by an ultrasound unit deployed in a renal artery in accordance with embodiments of the invention.

FIG. 7 illustrates an embodiment of an ultrasound arrangement for denervating renal vasculature that contributes to renal sympathetic nerve activity in accordance with the invention. According to this embodiment, an ultrasound unit 50 is shown deployed in a patient's renal artery 12 and equipped with an ultrasonic emitter 52 configured to deliver focused acoustic energy to target tissue 49 that includes renal nerves 14 and/or renal or aortic ganglia 24/22. Various emitters 52a-52c are shown for illustrative purposes that have different possible beam patterns 58, including concave, convex, and linear beam patterns.

The ultrasound unit 50 may incorporate one or more of the same or disparate emitters 52a-52c to achieve desired acoustic energy characteristics, including a desired acoustic beam pattern or geometry, beam spread, beam divergence, and/or focal length, among other characteristic. Various mechanical and electronic beam shaping or beamforming apparatuses and techniques may be used to achieve desired acoustic energy characteristics. Different acoustic energy characteristics may be required or desired depending on a number of factors, including the separation distance between the ultrasound unit 50 and the target tissue (e.g., short range vs. long range targets; intravascular vs. transvascular targets) and modes of ultrasound unit operation (e.g., scan vs. ablation modes), among others.

In various embodiments, the ultrasound unit 50 incorporates an acoustic transducer arrangement 52a that emits acoustic energy in a generally conical-shaped beam 58a that converges at a generally elliptical focal region 37 situated at a desired depth of focus, l. The ultrasonic unit 50 is positioned so that the focal region 37 is coincident with respect to target tissue that includes renal nerve fibers 14 and/or ganglion tissue 24/22. After properly positioning the ultrasonic unit 50, focused ultrasonic energy (e.g., HIFU) is transmitted to the focal region 37 at the desired depth, l, to destroy the renal nerve fibers 14 and/or ganglion tissue 24/22 within the focal region 37. An acoustic transducer arrangement 52 of the ultrasonic unit 50 may have a fixed focal length, but preferably has a variable focal length.

To ensure protection of non-targeted renal artery and aortal tissue layers during HIFU or other form of ultrasonic renal denervation, various temperature control apparatuses may be used to enhance cooling at or proximate to the ultrasound unit 50. In general, the maximum temperature of the inner wall of the renal artery may be kept below some target temperature, such as 50° C., by providing heat transfer sufficient to limit the temperature rise at the inner artery wall, while allowing for a temperature increase above the target temperature within the artery wall tissue sufficient to permanently disrupt the renal nerve fibers/ganglia.

Figure 8:
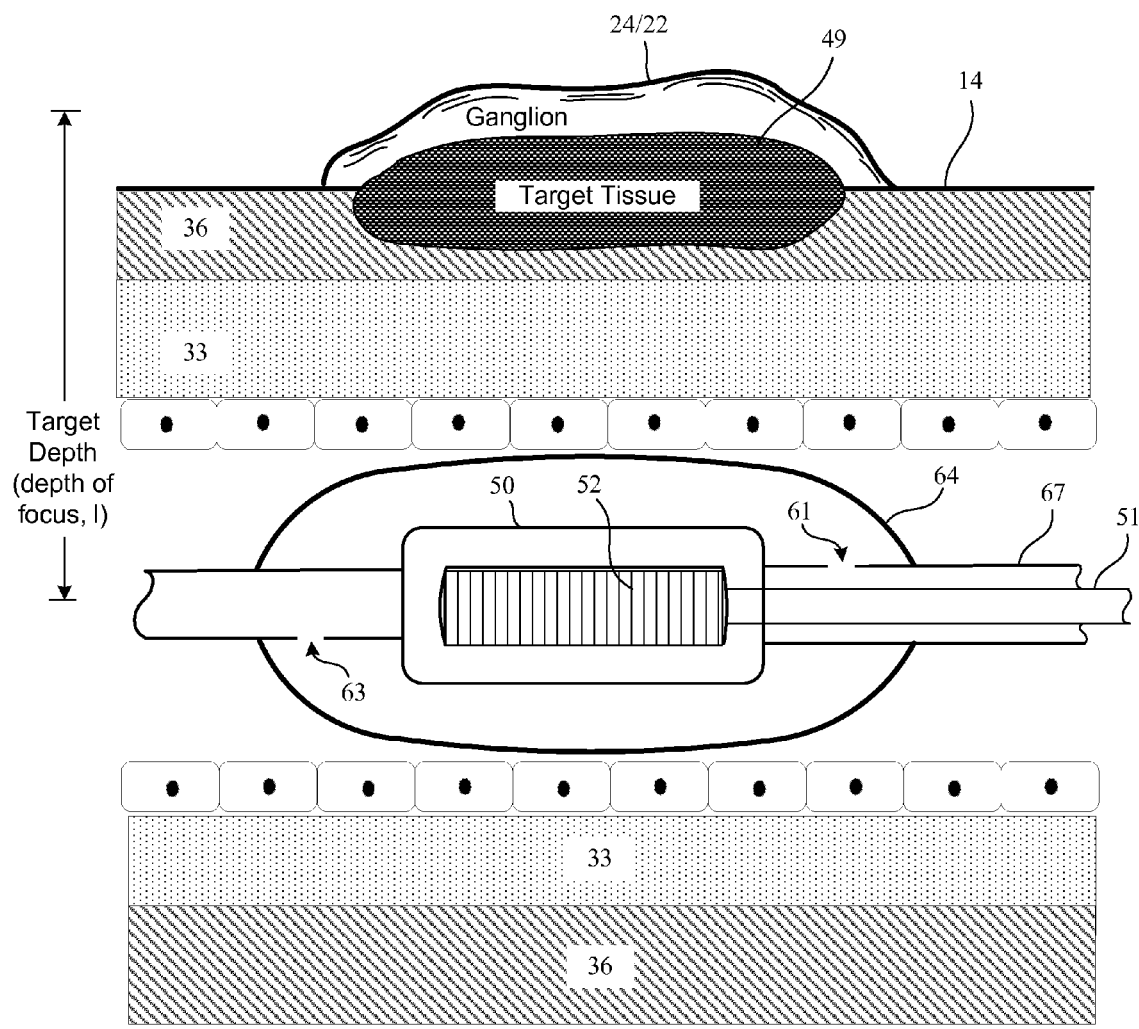
FIGS. 8-10 illustrate an ultrasound unit and a balloon arrangement deployed in a renal artery in accordance with embodiments of the invention.

FIG. 8 illustrates an embodiment of an ultrasound arrangement for denervating renal vasculature that contributes to renal sympathetic nerve activity in accordance with the invention. According to this embodiment, an ultrasound unit 50 is configured for deployment within a balloon 64. The ultrasound unit 50 is shown disposed at a distal end of a catheter 51 and situated within the balloon 64 at a relatively central location. When expanded, the balloon 64 contacts the inner wall of the renal artery and stabilizes the ultrasound unit 50 at a desired location and orientation within the balloon (e.g., central location oriented axially along the balloon's central axis).

The balloon 64 may be configured to allow blood flow within the renal artery to provide cooling of the artery wall during an ablation procedure. A perfusion balloon (e.g., fluted or channeled balloon) or a fluid diversion arrangement (e.g., longitudinal inlet/outlet ports or channels) may be used to allow perfusion of blood to cool the artery wall during ultrasonic ablation.

In other embodiments, the ultrasound unit 50 may be incorporated into a balloon 64 which can be expanded to the internal diameter of the renal artery, so that the balloon blocks or partially blocks the flow of blood. The balloon 64 can be filled with a liquid that provides good acoustic coupling between the ultrasound unit 50 and balloon wall, such as saline, D5W, or a suitable cryogenic liquid. The liquid used to fill the balloon 64 preferably allows acoustic energy emitted from the ultrasonic emitter 52 to efficiently propagate through the liquid medium and through the balloon before impinging on renal artery tissue. The liquid in the balloon 64 is preferably acoustically "transparent" to the frequencies of the acoustic energy emitted by the ultrasound unit 50.

It is desirable that the liquid supplied to the balloon 64 not be toxic and should be soluble in blood to minimize possible embolic damage if the liquid should leak out of the balloon 64. The liquid in the balloon 64 may be circulated with open or closed irrigation to keep the inner wall of the artery from being heated above 50° C. during an ultrasonic ablation procedure, while the internal tissue and nerve/ganglion of the renal artery is heated above 50° C., to disrupt the nerve function while avoiding stenosis of the renal artery wall due to the response to burn injury. The liquid may be a cooling liquid, such as a cryogenic liquid.

In the embodiment shown in FIG. 8, the balloon 64 includes an inlet manifold 61 and an outlet manifold 63 that facilitate pressurization, depressurization, and circulation of a cooling or cryogenic liquid within the balloon 64. The balloon 64 may comprise a single or multiple balloon structure, with appropriate lumens provided in the catheter 51 or other catheter of the treatment apparatus. One or more temperature sensors (not shown) are provided at the balloon 64 to monitor temperature near or at the vessel wall.

Figure 9:
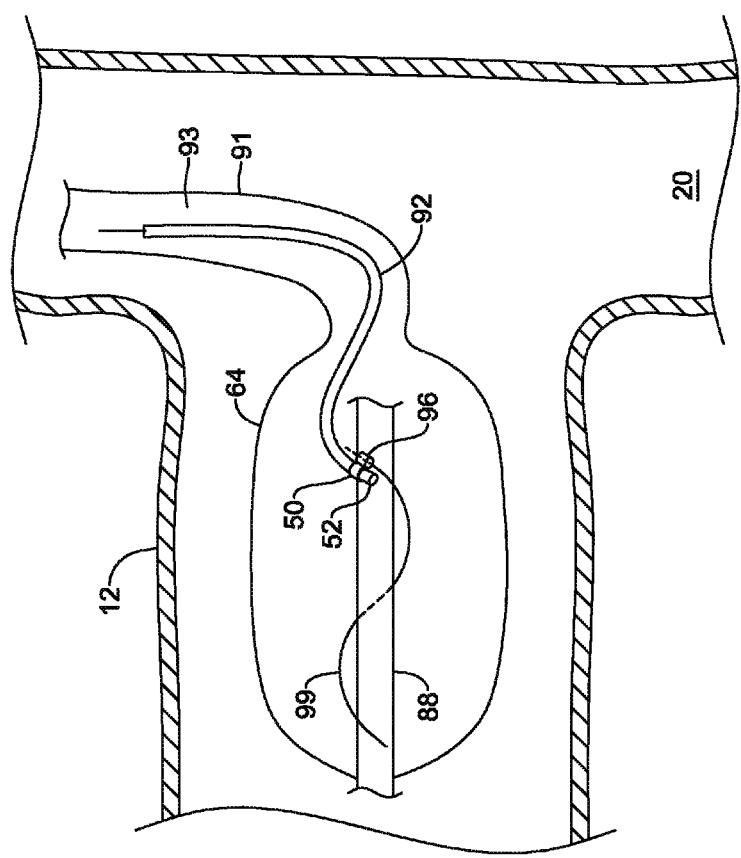
Figure 10:
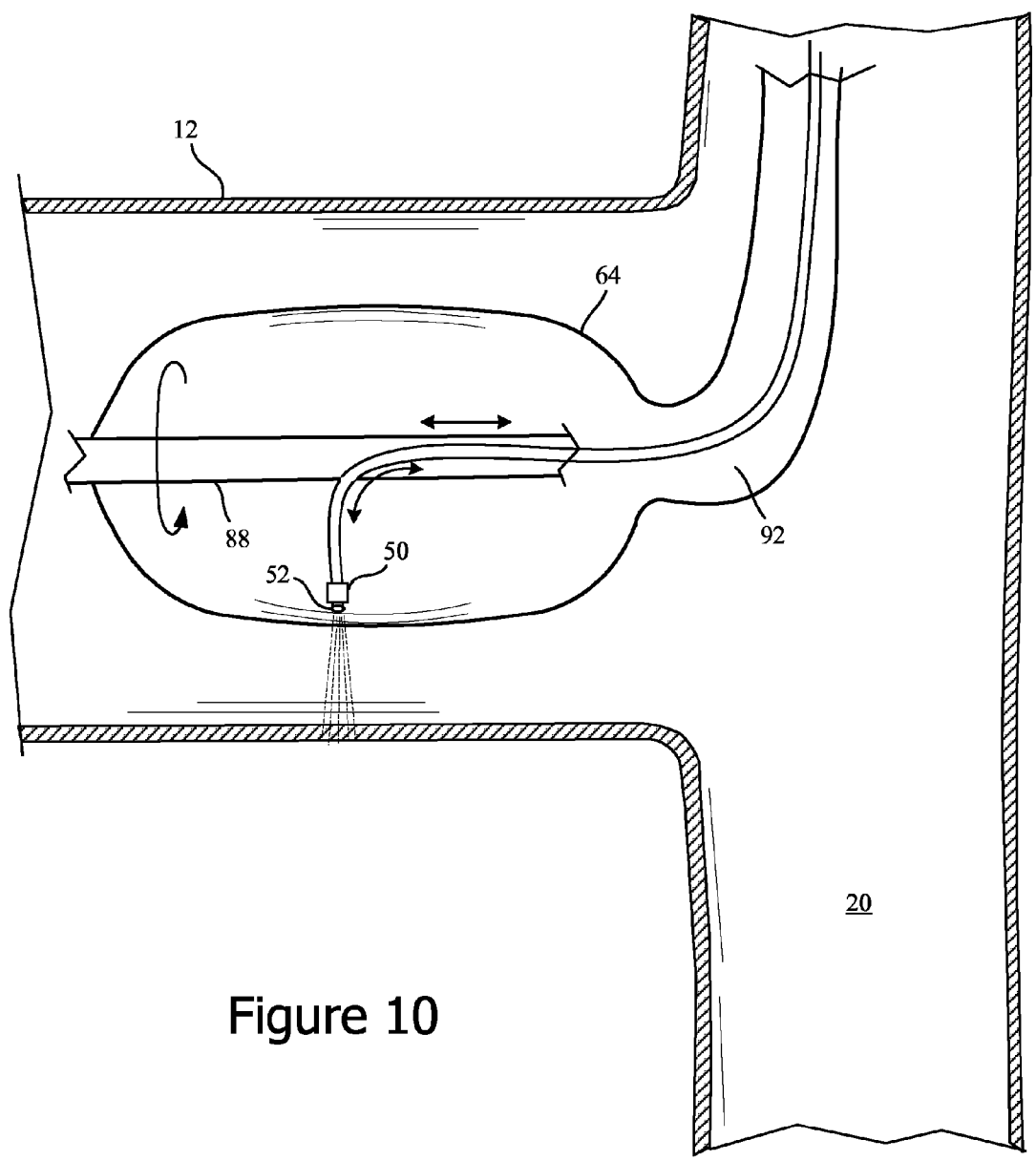

An advantage of using a balloon 64 of the type shown in FIG. 8 is that the ultrasound unit 50 can be translated and rotated without contacting the renal artery wall. In some embodiments, the shaft 67 can incorporate a spiral rail that forces the ultrasound unit 50 (or at least the emitter 52) to travel a helical path as it is advanced and retracted through the renal artery lumen. An illustrative example of such a configuration is shown in FIG. 9, which is described in detail hereinbelow. In other embodiments, the emitter 52 of the ultrasound unit 50 is oriented off-axis with respect to the longitudinal axis of the shaft 67. For example, the emitter 52 may be oriented at an angle of about 45° to about 135° relative to the longitudinal axis of the shaft 67, with about 90° representing a preferred orientation. An illustrative example of such a configuration is shown in FIG. 10, which is described in detail hereinbelow.

According to various embodiments, the balloon 64 or a balloon separate from the ultrasound unit 50 may be implemented to deliver cryogenic therapy to innervated renal vasculature in combination with ultrasonic ablation therapy. In some embodiments, a balloon arrangement separate from the ultrasonic device 50 is used so that a wider range of cryogenic fluids (liquids and gasses) can be used to achieve desired therapeutic temperatures. For embodiments that use a separate cryoballoon arrangement, the cryogenic fluid that fills the balloon need not be an acoustic coupling fluid, since the ultrasound unit 50 is not situated within the cryoballoon. It is noted that the ultrasound unit 50 may be situated in a separate balloon (e.g., balloon 64), and that the separate cryoballoon and balloon 64 within which the ultrasound unit 50 is situated may be supported by a common catheter or separate catheters.

Suitable cryoballoons include those that can cause renal tissue freezing and/or denervation at therapeutic temperatures ranging between approximately 0° C. and approximately −180° C. For example, embodiments of a cryoballoon may be implemented to cause renal tissue freezing and/or denervation with temperatures at the renal nerves ranging from approximately 0° C. to approximately −30° C. at the higher end, and to about −140° C. to −180° C. at the lower end. These therapeutic temperature ranges may vary based on the combined therapeutic effect of delivering cryogenic and ultrasonic denervation therapy energy to innervated target tissue of the renal artery and/or aorta. A variety of useful cryogenic fluids may be employed, including saline, a mixture of saline and ethanol, Freon or other fluorocarbons, nitrous oxide, liquid nitrogen, and liquid carbon dioxide, for example.

According to another embodiment, an ultrasound unit 50 of the type shown in FIG. 8 (with or without a balloon, such as balloon 64) can include a lumen arrangement for transporting a thermal transfer fluid to provide local cooling (not freezing) of the intimal layer adjacent the ultrasound unit 50. In this embodiment, the catheter shaft 61 may incorporate one or more cooling lumens that interact directly with the adjacent intimal layer to counteract the application of higher intensity energies targeted for renal nerves that are further away or deeper in the artery wall. In other embodiments, a separate cooling catheter arrangement may be employed to provide direct localized cooling to the renal artery wall.

The balloon 64 shown in FIG. 8 and in other figures is preferably a very low pressure balloon system. It is desirable to achieve minimal contact between the balloon 64 or other stabilizing arrangement and the inner wall of the renal artery in order to avoid injuring the sensitive endothelium of the artery. Very low pressure balloon systems can serve to provide minimal contact with the renal artery's inner wall and stabilization of the ultrasound unit 50.

The balloon 64 or other stabilizing balloon can be constructed as a compliant balloon as is known in the art. For example, balloon 64 may comprise a compliant material configured to enable the balloon 64 to inflate under a very low pressure, such as about 1 to 2 pounds per square inch (PSI) or less (e.g., 0.5 PSI or less) above an ambient pressure that is adjacent to and outside the balloon 64. The compliancy of balloon 64 preferably results in little or negligible circumferential force applied to the vessel wall, while readily allowing the balloon to conform to irregularities in the shape of the tissue of the aortal/renal vasculature, which results in more efficient delivery of cooling or cryotherapy to tissues surrounding the target tissue (i.e., renal nerve fibers and renal ganglia).

All or a portion of the balloon 64 may be made of a highly compliant material that elastically expands upon pressurization. Because the balloon 64 elastically expands from a deflated state to an inflated state, the balloon 64 has an extremely low profile in the deflated state when compared to non-compliant or semi-compliant balloons. According to some embodiments, use of high compliance materials in the construction of the balloon 64, in combination with a hinge mechanism 56 built into the catheter 51 (see, e.g., hinge 356 shown in FIG. 20), provides for enhanced efficacy and safety when attempting to navigate a catheter 51 supporting an ultrasound unit 50 and one or more balloons through a nearly 90 degree turn from the abdominal aorta 20 into the ostium of the renal artery 12.

Suitable materials for constructing all or a portion of the balloon 64 or other balloon include thermoplastic or thermoplastic elastomers, rubber type materials such as polyurethanes, natural rubber, or synthetic rubbers. The resulting balloon may be crosslinked or non-crosslinked. Other suitable materials for constructing all or a portion of the balloon 64 include silicone, urethane polymer, low durometer PEBAX, or an extruded thermoplastic polyisoprene rubber such as a low durometer hydrogenated polyisoprene rubber. These and other suitable materials may be used individually or in combination to construct the balloon 64. Details of various materials suitable and configurations for constructing a balloon 64, a stabilizing balloon or other balloon arrangement according to various embodiments are disclosed in commonly owned U.S. Pat. No. 7,198,632, U.S. application Ser. Nos. 12/980,952, and 12/980,972, which are incorporated herein by reference.

Embodiments of the invention may incorporate selected balloon, catheter, lumen, control, and other features of the devices disclosed in the following commonly owned U.S. patents and published patent applications: U.S. Patent Publication Nos. 2009/0299356, 2009/0299355, 2009/0287202, 2009/0281533, 2009/0209951, 2009/0209949, 2009/0171333, 2008/0312644, 2008/0208182, and 2008/0058791, and U.S. Pat. Nos. 5,868,735, 6,290,696, 6,648,878, 6,666,858, 6,709,431, 6,929,639, 6,989,009, 7,022,120, 7,101,368, 7,172,589, 7,189,227, 7,198,632, and 7,220,257, which are incorporated herein by reference. Embodiments of the invention may incorporate selected balloon, catheter, and other features of the devices disclosed in U.S. Pat. Nos. 6,355,029, 6,428,534, 6,432,102, 6,468,297, 6,514,245, 6,602,246, 6,648,879, 6,786,900, 6,786,901, 6,811,550, 6,908,462, 6,972,015, and 7,081,112, which are incorporated herein by reference.

In various embodiments, the balloon 64 comprises a cryoballoon (or a separate cryoballoon may be used as previously discussed) and the ultrasound unit 50 includes one or more ultrasonic emitters 52. The balloon 64 and ultrasound unit 50 cooperate to deliver acoustic and thermal energy to target tissue 49. In some embodiments, the ultrasound unit 50 comprises an ultrasonic emitter 52 that creates lesions in the artery wall primarily through disruptive heating of target tissue. In other embodiments, the ultrasound unit 50 comprises an ultrasonic emitter 52 that creates lesions in the artery wall primarily by production of cavitation bubbles, which work to mechanically disrupt nerve fibers and ganglia with the bubbles implode or explode.

According to various embodiments, a denervation therapy procedure using the apparatus shown in FIG. 8 involves selectively freezing and heating (and optionally thawing) target tissue 49 that includes renal nerves 14 and/or ganglia 24/22. For example, target innervated tissue 49 is frozen using a cryoballoon 64. Before the target tissue 49 thaws, acoustic energy is transmitted to the target tissue 49 by the ultrasound unit 50 to fracture the renal nerve fibers and nerve sheaths located in the adventitia or vasa vasorum externae, thereby permanently terminating renal sympathetic nerve traffic along the treated renal nerve structures. A detailed discussion of renal nerve structures and degrees of nerve disruption that can be achieved using embodiments of the invention is provided in previously cited U.S. application Ser. No. 12/980,952.

The cryoballoon 64 and/or catheter apparatus is preferably configured to allow blood to flow at or near the inner vessel wall after cryotherapy has been delivered to allow for local heating of the endothelium and adjacent tissue (e.g., intima and media tissue) while the adventitia remains frozen. Acoustic energy is preferably transmitted to the still-frozen adventitia layer (at least to deeper layers near the vessel's outer wall) to permanently disrupt renal nerves and ganglia included in the frozen tissue.

An advantage of using combined cryogenic and ultrasonic therapies for denervating renal artery and aortal tissue is that blood coagulation and embolization associated with RF ablation is avoided. Another advantage is that nerve regeneration over time that can occur when using cryotherapy alone is prevented, because of the fracturing of the renal nerve sheath resulting from mechanical disruption when using cavitation ultrasonic denervation therapy, or from thermal necrotic coagulation when using thermal ultrasonic denervation therapy, which permanently disrupts renal nerve sheaths.

With reference to FIG. 9, there is shown an embodiment of an ultrasonic ablation apparatus which includes an ultrasound unit 50 incorporated into a balloon 64. The ultrasonic ablation apparatus shown in FIG. 9 may include an imaging capability. The balloon 64 may be affixed adjacent to a distal end of a first catheter 91. The first catheter 91 may include a central shaft 88 disposed within a lumen 93 of the first catheter 91 and within an interior volume of the balloon 64. A spiral rail 99 may be disposed about an outer surface of the central shaft 88 adjacent to a distal end of the central shaft 88. In some instances, the spiral rail 99 may be mounted on the central shaft 88 such that it extends around the entire circumference of the central shaft 88. In other instances, the spiral rail 99 may extend around only a portion of the circumference of the central shaft 88. The ultrasound unit 50 and/or emitter 52 may be disposed adjacent to a distal end of a second catheter 92. The second catheter 92 may be disposed within the lumen 93 of the first catheter 91 and slidable relative to the first catheter 91 such that the ultrasound unit 50 may be moved along the spiral rail 99. An advantage of using a balloon 64 of the type shown in FIG. 9 is that the translation and rotation of the ultrasound unit 50 may be accomplished by drawing or sliding the ultrasound unit 50 along a spiral rail 99 mounted on a central shaft 88 of the balloon 64. A keyed channel arrangement 96, for example, may be disposed at the distal end of the catheter 92 supporting the ultrasound unit 50, which receives and captures the spiral rail 99 such that drawing or sliding the second catheter 92 may cause the ultrasound unit 50 to follow the spiral path of the spiral rail 99.

The emitter 52 of the ultrasound unit 50 may be orientated at a desired angle relative to the longitudinal axis of the shaft 88 or relative to the rail 99. For example, the ultrasound unit 50 may be orientated at an angle ranging between 0 and 90 degrees relative to the longitudinal axis of the shaft 88 or the rail 99. With the ultrasound unit 50 moving axially along a spiral path defined by the rail 99 inside the balloon 64, no scraping of the renal artery wall 12 will occur. The catheter 92 is preferably translated along the rail 99 causing the ultrasound unit 50 to rotate and create a spiral burn, which interrupts any neural transmissions passing longitudinally within the wall of the renal artery 12. As discussed above, the balloon 64 may be filled with an acoustically transparent liquid, such as a cooling liquid.

FIG. 10 illustrates an ultrasonic ablation apparatus, which includes an ultrasound unit 50 situated at a distal end of a catheter 92, incorporated into a balloon 64 in accordance with various embodiments of the invention. The ultrasonic ablation apparatus of FIG. 10 may include an imaging capability.

In the embodiment shown in FIG. 10, the ultrasound unit 50 at the distal end of a catheter 92 is oriented off-axis with respect to the longitudinal axis of the shaft 88. In FIG. 10, the emitter 52 of the ultrasound unit 50 is shown oriented about 90° relative to the longitudinal axis of the shaft 88. It is understood that other emitter orientations may be desirable.

For example, the ultrasound unit 50 may be oriented at an angle of about 45° to about 135° relative to the longitudinal axis of the shaft 88. Also, the emitter 52 may be biased more toward the shaft 88 than the outer surface of the balloon 64. The ultrasound unit 50 may be configured to extend from and retract into the shaft 88 under user or robotic control, which may be of particular benefit when expanding and contracting the balloon 64. The shaft 88 and the ultrasound unit 50 may be translatable and/or rotatable within the balloon 64.

FIG. 11 shows an embodiment of an extracorporeal denervation arrangement for denervating renal vasculature that contributes to renal sympathetic nerve activity in accordance with the invention. According to this embodiment, an emitter 52 of a lithotripsy machine 35 is shown positioned at or above the patient's skin 47 proximate a renal artery 12. The lithotripsy machine 35 generates high-energy shockwaves that are directed to target tissue 49 to fragment renal nerve and ganglia tissue structures (e.g., sheaths of nerve fibers located in the adventitia, vasa vasorum, or in ganglia). The lithotripsy machine 35 may be configured as an extracorporeal shockwave lithotripsy (ESWL) machine, for example.

The lithotripsy machine 35 uses one or both of x-rays and ultrasound scanning to locate target tissue that includes innervated renal vasculature. The lithotripsy machine 35 generates an acoustic shockwave, which is transmitted into the body via the emitter 52. Embodiments of an extracorporeal lithotripsy system for denervating renal and aortal tissue may incorporate components and functionality disclosed in U.S. Pat. No. 6,123,679, which is incorporated herein by reference.

According to other embodiments, an intracorporeal lithotripsy system may be used to denervate renal and aortal vasculature that contributes to renal sympathetic nerve activity. An intracorporeal lithotripsy system typically includes an endoscope that is percutaneously advanced to a location within the body proximate a renal artery or the abdominal aorta. An acoustic shockwave is transmitted from an emitter 52 of the endoscope into the renal artery or the abdominal aorta to disrupt innervated target tissue. Embodiments of an intracorporeal lithotripsy system for denervating renal and aortal tissue may incorporate components and functionality disclosed in commonly owned U.S. Pat. No. 5,906,623, which is incorporated herein by reference.

In other embodiments, an intracorporeal laser lithotripsy or lasertripsy system may be used to denervate renal and aortal vasculature that contributes to renal sympathetic nerve activity. An intracorporeal lasertripsy system of the present invention includes a laser source and an optical fiber that extends along a longitudinal axis of a rigid or flexible endoscope. Laser light of an appropriate wavelength and power is transmitted from the optical fiber to a focal point or region that includes innervated renal tissue. Various types of lasertripsy systems and laser sources may be used, including systems that include a pulsed dye laser, an alexandrite laser, a neodymium laser, and a holmium laser, for example. Embodiments of an intracorporeal lasertripsy denervation system for denervating renal and aortal tissue may incorporate components and functionality disclosed in commonly owned U.S. Provisional Application Ser. No. 61/324,163, and in commonly owned U.S. Pat. No. 7,104,983, both of which are incorporated herein by reference.

In accordance with various embodiments employing acoustic or laser lithotripsy, and as further shown in FIG. 11, an intravascular cryocatheter or cryoballoon 64 is deployed within the renal artery to freeze target tissue 49 prior to delivering lithotripsy therapy to the target tissue 49. Freezing the target tissue 49 prior to delivering lithotripsy therapy enhances disruption of target nerve structures by the shockwaves impinging on the frozen target tissue 49. Freezing of the target tissue 49 in the context of the embodiment illustrated in FIG. 11 may be accomplished using various devices and techniques described herein.

FIGS. 12A-12D show different embodiments of an ultrasound unit 50 configured for denervating renal vasculature that contributes to renal sympathetic nerve activity in accordance with the invention. In the embodiment shown in FIG. 12A, the emitter 52 of the ultrasound unit 50 includes an aperture 65 through which an acoustic energy beam 62 passes. The aperture 65 may be a void, a lens arrangement, or acoustic coupling material that allows for efficient transmission of the acoustic energy beam 62 from the emitter 52 and out of the ultrasound unit 50. The aperture 65 and emitter 52 are situated at a desired location of the ultrasound unit 50, and can be "aimed" at target tissue by rotating and translating the catheter 51 to which the ultrasound unit 50 is attached, or the ultrasound unit 50 relative to the catheter 51 in embodiments where the ultrasound unit 50 is movable relative to the catheter 51, either manually or robotically.

According one approach, the catheter 51 can be translated and rotated along the rail 99 to cause the ultrasound unit 50 to create a spiral burn. In another approach, an ultrasound unit 50 equipped with a focused ultrasonic emitter 52 can be rotated to create a circular or cylindrical burn without incurring undue risk of stenosis of the renal artery 12.

One advantage of creating a circular or cylindrical lesion in the renal artery wall is that the longitudinal extent of the lesion is limited, which allows for repeated denervation procedures to be performed at untreated regions of the renal artery without undue risk of artery stenosis. For example, a circular or cylindrical lesion may be created near the ostium of the renal artery, leaving the majority of renal artery tissue untreated. Should additional renal denervation be required, a subsequent circular or cylindrical lesion may be created near the center or distal end of the renal artery. A mapping of renal artery lesion locations for a given patient may be stored to aid in avoiding previously treated regions of the artery when performing a subsequent ablation procedure.

Figure 12A:
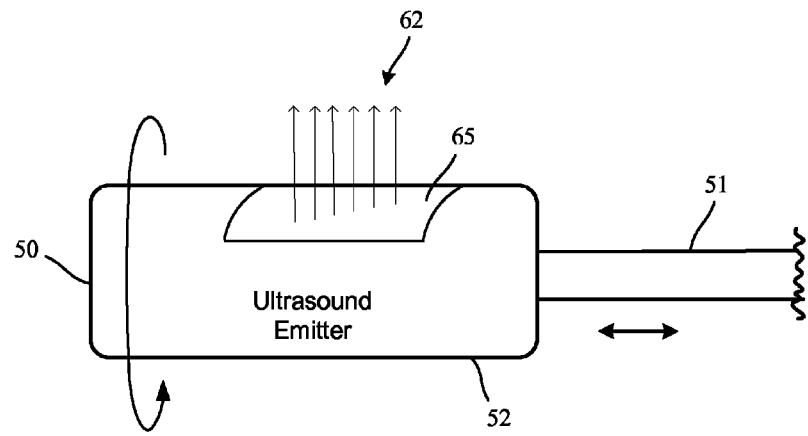
FIGS. 12A and 12B illustrate ultrasound units having single and distributed ultrasonic elements in accordance with embodiments of the invention.
Figure 12B:
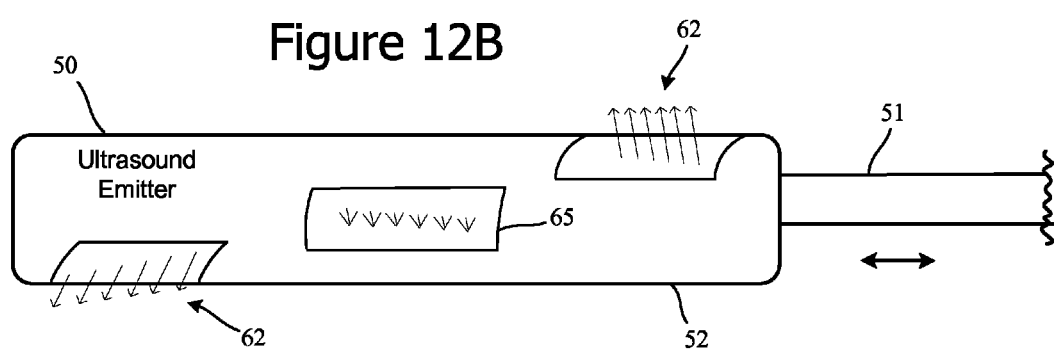

FIG. 12B shows an ultrasound unit 50 comprising a multiplicity of apertures 65 and emitters 52. The apertures 65 and emitters 52 are preferably situated so that their beam patterns 62 collectively impinge on renal artery tissue in a generally spiral pattern and at target depths in the renal artery wall. The spiral lesion may either be continuous or a sequential and overlapping line of ablated spots.

The ultrasound unit 50 shown in FIG. 12B advantageously facilitates a "one-shot" denervation therapy of the renal artery or other vessel in accordance with embodiments of the present invention. The term "one-shot" treatment refers to treating the entirety of a desired portion of a vessel without having to move the treatment implement or arrangement to other vessel locations in order to complete the treatment procedure (as is the case for a step-and-repeat denervation therapy approach).

A one-shot treatment approach according to the embodiment shown in FIG. 12B advantageously facilitates delivery of denervation therapy that treats at least one location of each nerve fiber extending along a target vessel, such as the renal artery, without having to reposition the ultrasound unit 50 during denervation therapy delivery. The embodiment of an ultrasound unit 50 shown in FIG. 12B allows a physician to position the ultrasound unit 50 at a desired vessel location, and completely treat the vessel without having to move the ultrasound unit 50 to a new vessel location.

It is noted that, in some embodiments, the ultrasound unit 50 can be coupled to the catheter 51 using a coupling arrangement that allows the ultrasound unit 50 to be rotated relative to the catheter 51. A manual or motorized apparatus may be controlled to cause rotation of the ultrasound unit 50 relative to the catheter 51. In other embodiments, the ultrasound unit 50 may be coupled to the catheter 51 such that rotation of the catheter 51 causes rotation of the ultrasound unit 50.

Figure 12C:
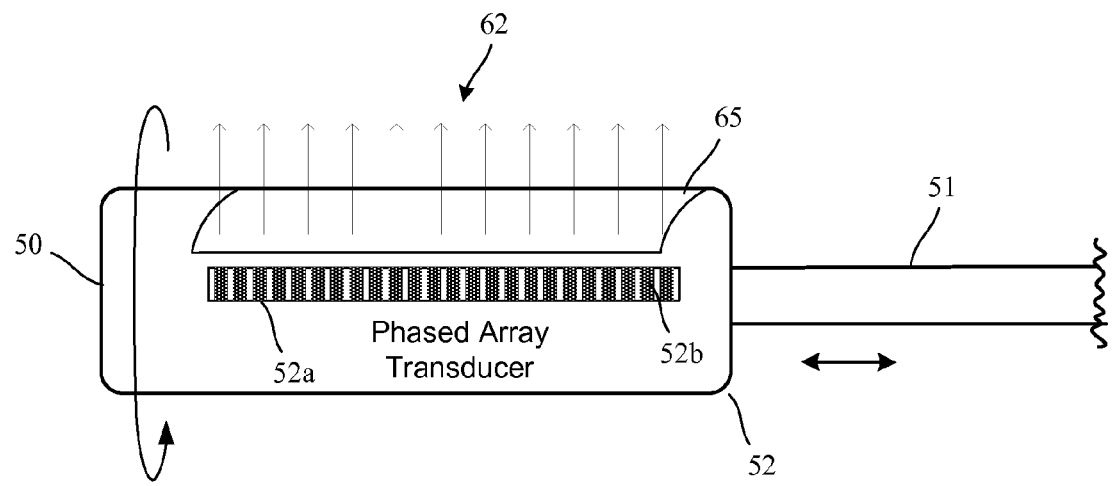
FIGS. 12C and 12D illustrate ultrasound units that include one or more acoustic phased array transducers in accordance with embodiments of the invention.
Figure 12D:
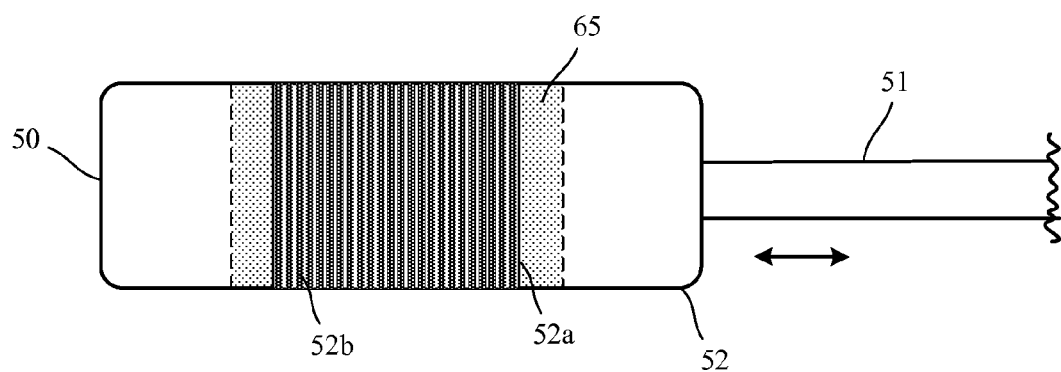

FIGS. 12C and 12D illustrate embodiments of an ultrasound unit 50 configured for denervating renal vasculature that contributes to renal sympathetic nerve activity in accordance with the invention. In the embodiments shown in FIGS. 12C and 12D, the emitter 52 of the ultrasound unit 50 includes an acoustic phased array transducer 52*a* which comprises a multiplicity of acoustic elements 52*b*. The phased array transducer 52*a* shown in FIG. 12C extends over a radial segment of the ultrasound unit's circumference, allowing an acoustic energy beam 62 to pass through an aperture 65 (e.g., lens arrangement) and impinge on target tissue. As can be the case in other embodiments, the emitter 52 of the ultrasound unit 50 may be aimed at target tissue by rotating and translating the catheter 51, or by moving the ultrasound unit 50 relative to the catheter 51, either manually or robotically.

In the embodiment shown in FIG. 12D, a phased array transducer 52*a* extends over all or nearly all of the ultrasound unit's circumference, allowing an acoustic energy beam 62 to pass through an annular aperture 65 (e.g., lens arrangement) and impinge on a circular or cylindrical target tissue region. After positioning the ultrasound unit 50 within the renal artery, for example, renal denervation can be conducted without having to translate or rotate the catheter 51 or ultrasound unit 50.

A cooling arrangement may be incorporated in the embodiments of FIGS. 12A-12D to ensure that the temperature of inner arterial or aortal wall tissue (e.g., intima, media) is limited to prevent thermal injury to this tissue. In embodiments that include focused acoustic transducers or transducer arrays, however, such cooling arrangement may not be required or desired, which can result in intravascular denervation apparatuses of reduced size and complexity.

Figure 13A:
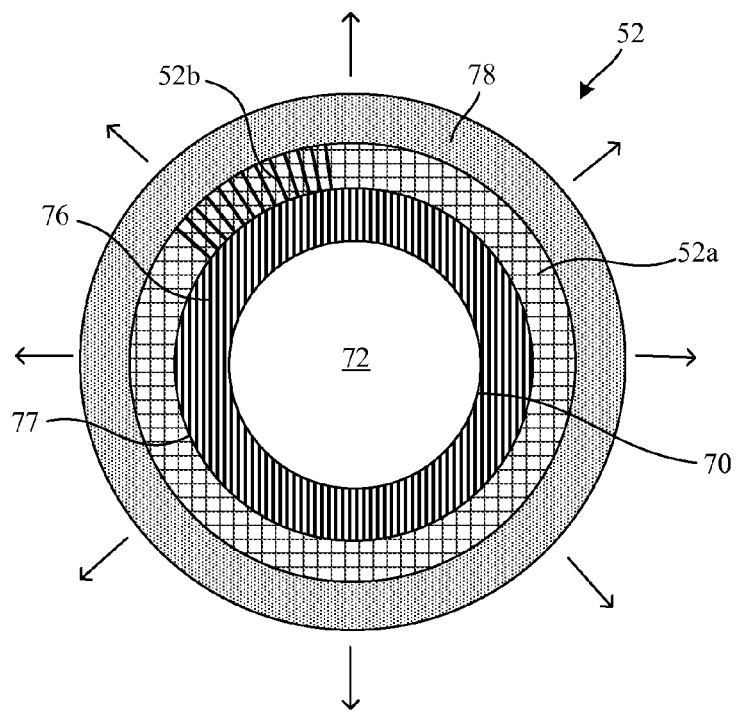
FIGS. 13A and 13B are sectional views of ultrasound units that include one or more acoustic phased array transducers in accordance with embodiments of the invention.
Figure 13B:
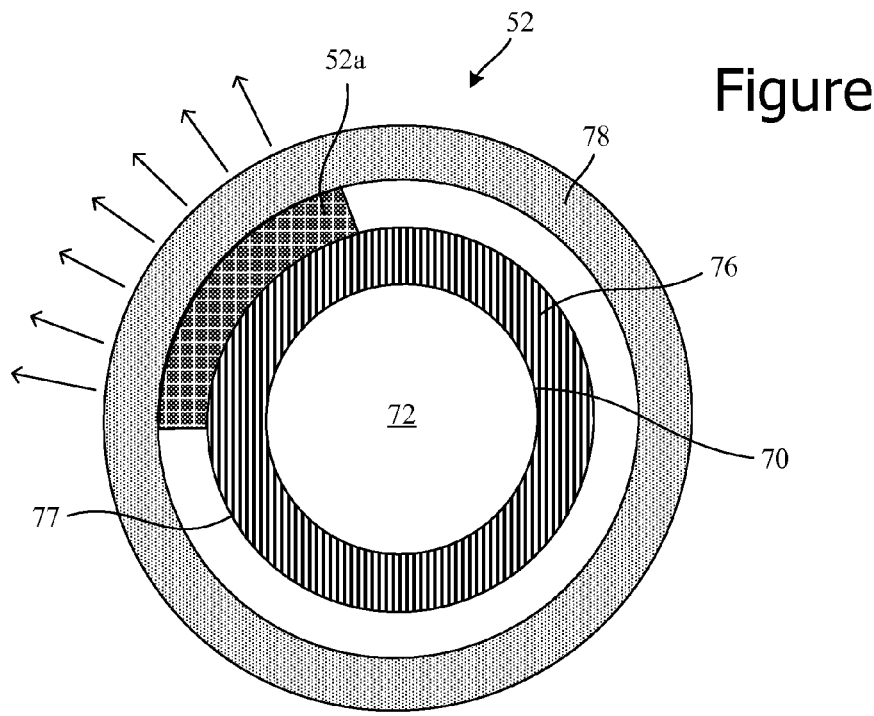
Figure 14:
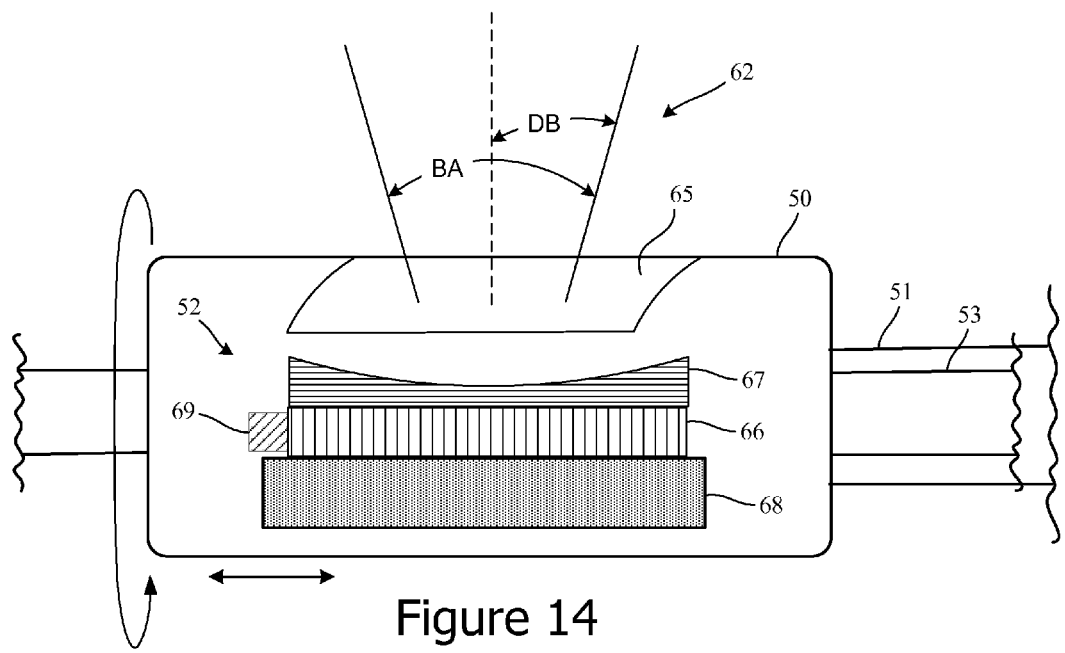
FIGS. 14 and 15 illustrate ultrasound units that include one or more acoustic transducers of varying configuration in accordance with embodiments of the invention.

Different embodiments of phased array acoustic emitter arrangements that can be incorporated in ultrasound units 50 of the invention are shown in FIGS. 13 and 14. Phased array transducers 52*a* are typically more effective than conventional planar or curved piezoelectric transducers and are well suited for high power ultrasonic ablation of innervated renal vasculature. The phased array transducers 52*a* comprise a number of individual ultrasonic elements 52*b*, often called "pixels," with each pixel having a respective wired connection to an electrical driver. By controlling the phases of each of the electrical drivers, an ultrasound beam can be electronically scanned in a target tissue location.

FIGS. 13A and 13B are sectional views of an ultrasonic emitter 52 comprising different configurations of phased array transducers 52*a* having a generally cylindrical shape in accordance with embodiments of the invention. The ultrasonic emitter 52 shown in FIG. 13A includes a phased array transducer 52*a* comprising a multiplicity of individual ultrasonic elements 52*b* supported by a flexible circuit substrate 77 and arranged in a spaced-apart relationship about the circumference of the ultrasonic emitter 52 (although only a few representative elements 52*b* are shown in FIG. 13A for clarity). In FIG. 13B, the ultrasonic emitter 52 includes a phased array transducer 52*a* comprising a multiplicity of individual ultrasonic elements 52*b* supported by a flexible circuit substrate 77 and arranged in a spaced-apart relationship about a radial segment of the circumference of the ultrasonic emitter 52.

In the embodiment shown in FIG. 13A, acoustic energy is emitted in a circular or cylindrical beam pattern, which provides for scanning and/or ablating of a circular or cylindrical target region of the renal artery or abdominal aorta. It is noted that the phased array transducer 52*a* shown in FIG. 13A need not extend along the entirety of the ultrasonic emitter's circumference, since the ultrasonic beam spread at the opposing ends has a laterally extending aspect. In the embodiment shown in FIG. 13B, acoustic energy is emitted in a partial circular or cylindrical beam pattern (e.g., <360°, such as 20°-90°), which provides for scanning and/or ablating of a partial circular or cylindrical region of renal artery or abdominal aorta target tissue.

Adjacent an outer circumference of the phased array transducer 52*a* is an acoustic lens 78, as is shown in FIGS. 13A and 13B. An acoustic coupling material or liquid may be disposed between the phased array transducer 52*a* and the acoustic lens 78. Adjacent an inner circumference of the phased array transducer 52*a* are one or more acoustic layers 76, which are in contact with a cylindrical backing member 72 that encompasses a supportive core 72.

The phased array transducer 52*a* shown in FIGS. 13A and 13B may be formed by dividing one or more larger piezoelectric blocks into two or more individual ultrasonic elements 52*b* supported by the flexible circuit substrate 77. Individual ultrasonic elements 52*b* are responsive to an appropriate electrical stimulus for generating acoustic energy in the ultrasonic frequency range. The number of individual ultrasonic elements 52*b* may vary significantly depending on transducer configuration and requirements.

For example, a HIFU ultrasonic emitter 52*a* that incorporates one or more ultrasonic phased array transducers 52*a* may include 10 or less ultrasonic elements 52*b* to as many as 1,000 elements 52*b* or more (e.g., $\geq 24$, $\geq 64$, $\geq 256$, $\geq 512$, $\geq 768$, or $\geq 1024$ individual elements 52*b* may be incorporated in ultrasonic phased array transducers 52*a* according to various embodiments).

HIFU phased array driving electronics can be adapted to control the phase and amplitude of individual ultrasonic elements 52*b* using an appropriate number of control channels. For example, a HIFU ultrasonic emitter 52*a* may include up to 1024 discrete ultrasonic elements 52*b* each controlled by a separate channel with 2 ns phase resolution, 8-bit amplitude resolution, operate over a frequency range of 1 to 5 MHz, and deliver between 8 and 15 W of power to each channel.

The use of a large number of ultrasonic elements and control channels allows for the elimination of mechanical motion components of conventional single-element and array HIFU systems. For example, a HIFU phased array transducer 52*a* that incorporates a large number of ultrasonic elements and channels can simulate movement of the array using various known subaperture focusing techniques. A HIFU phased array transducer 52*a* may be electronically controlled to generate sufficiently high HIFU intensities at foci of spherical or cylindrical geometries and at a desired depth within innervated renal tissue.

It is noted that curvilinear or convex sector phased arrays may be used as an alternative to, or in concert with, a linear phased array configuration. A curvilinear phased array operates in the same manner as the linear array in that the scan lines are directed perpendicular to the transducer face. The acoustic beams generated by curvilinear or convex sector phased arrays are typically focused, rather than steered.

The power level and frequency range may be selected to provide for both scanning (e.g., lower power) and ablating (e.g., higher power) of innervated renal tissue. Although the acoustic power and transducer efficiency will vary among ultrasound transducer implementation, it is desirable that power levels corresponding to focal peak intensities equal to or greater than about 2000 W/cm$^2$ in target tissue be achieved, which are capable of producing coagulative necrosis in the target tissue.

With reference to FIG. 14, an ultrasound unit 50 includes an ultrasonic transducer 52 that can operate in a scan mode, a thermal ablation mode, or a cavitation ablation mode. As is shown in FIG. 14, the transducer 52 includes a transducer element 66 (e.g., a piezoelectric element), a focusing lens 67, and acoustic material 68 which can be configured as an acoustic backing for the transducer 52.

The diameter and frequency of the transducer element 66 and the characteristics of the focusing lens 67 on the front of the transducer element 66 are preferably selected to maximize the intensity of acoustic power in the wall of the renal artery, which makes efficient use of the available power, reduces collateral damage, and makes the lesion relatively insensitive to small changes in the spacing from the transducer face to the artery wall. A temperature sensing element 69 may be provided and positioned to contact the transducer element 66 to monitor its temperature and prevent overheating. An acoustic backing layer 68 may be provided on the transducer element 66 to broaden the bandwidth of the transducer element 66 and to minimize the need for the ultrasound driver (not shown) to adapt the drive frequency to the ultrasound unit 50, which is typically a disposable element.

As was discussed above, the transducer element 66 may be operated in a scan mode, such as an A-scan mode or a B-scan mode as is understood in the art. Operating in the scan mode allows the system computer to diagnostically detect the range to the artery wall and potentially the thickness of the wall, and adapt the ultrasonic power and velocity of catheter translation so that a lesion of desired depth can be accomplished by the computer in the ultrasonic power drive unit.

Operating the ultrasound unit 50 in the scan mode allows the physician to see the lesion forming and estimate its depth intermittently or continuously. For example, the transducer element 66 may transmit continuously for a period during which the tissue in range will heat up. The transducer element 66 can then transmit a relatively short pulse and "listen" for the echoes as the system functions as an A-scan ultrasonic imager. The transducer element 66 can then detect the artery walls, lesion depth, and bubbles resulting from disruptive cavitation within the target tissue, and adjust the power strategy as desired. The transducer element 66 can then continue to transmit continuously for a period of time at the same or a modified transmit power.

It is noted that the ultrasound unit 50 may incorporate multiple transducers 52. In these configurations, some of the transducers 52 can operate continuously in a scan mode, while other transducers 52 can be operated continuously, intermittently, or sequentially in an cavitation ablation mode. For example, an ultrasound unit 50 may incorporate multiple transducers 52 that are arranged to produce a spiral lesion at the desired depth in the wall of the renal artery while the ultrasound unit 50 remains stationary within the lumen of the renal artery. This configuration provides for a "one-shot" denervation therapy approach in accordance with various embodiments of the invention.

With further reference to FIG. 14, the transducer 52 according to various embodiments includes a planar disk transducer element 66. As shown, the disk transducer 52 is supported within the housing of the ultrasound unit 50 which may have a cylindrical shape. The ultrasound unit 50 in this configuration can be translated longitudinally and rotated relative to a shaft 53 by appropriate manipulation of the catheter 51 to which the ultrasound unit 50 is connected. By properly translating and/or rotating the ultrasound unit 50, the location of the ablation moves, so that a spiral ablation or series of spot ablations may be made in the renal wall artery at the desired depth.

With a planar disk transducer 52, the ultrasound intensity is approximately constant near the transducer 52 and then drops faster as the range exceeds the diameter of the disk transducer element 66. A mechanism is preferably employed to stabilize the disk transducer element 66 so that its plane is parallel to the renal artery. It is also preferably to maintain the distance between the disk transducer element 66 and the artery wall approximately constant as the disk transducer 52 is translated and rotated.

The planar disk transducer 52 shown in FIG. 14 is a very practical design which can produce a relatively controllable burn width and depth as the disk transducer 52 is translated and displaced to produce a spiral burn inside the renal artery wall at the desired depth.

The beam angle of an ultrasonic disk transducer 52 will be normal to the disk transducer element 66 and centered on the axis of the disk transducer element 66. The beam angle, BA, shown in FIG. 14 can be characterized by:

$$\sin\theta = 1.2 V/(DF)$$

where theta is the half angle of the diverging beam (DB) in the far field, V is the sound velocity in the material, D is the diameter of the transducer element 66, and F is the frequency of the transducer 52.

Figure 15:
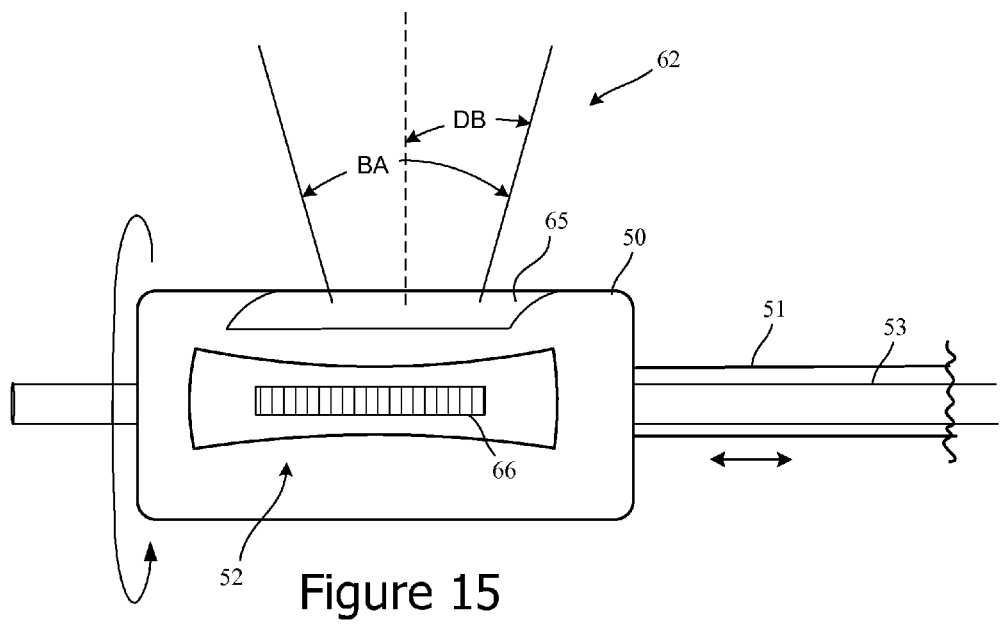

FIG. 15 shows another embodiment of an ultrasound unit 50 that includes a barrel shaped cylindrical ultrasonic transducer 52 that is configured to operate at least in a cavitation ablation mode. The barrel shaped cylindrical ultrasonic transducer 52 may also be operated in other modes, including a scan mode as discussed previously. In the configuration shown in FIG. 15, the hollow cylindrical barrel shaped transducer 52 rides over a central shaft 53 to treat the desired location on the renal artery. If not masked with acoustic reflector material, the transducer 52 will treat a complete 360° ring of tissue. If masked with an acoustic reflector material, the treatment will cover only part of the artery wall circumference.

Rotating the barrel shaped transducer 52 controls which angular section of the renal artery will be treated. Translating a masked barrel shaped transducer 52 will produce a spiral lesion if continuously on, or a spiral of spots within the renal artery wall if powered intermittently. It is desirable to use a centering mechanism to insure that the barrel shaped transducer 52 is centered in the lumen of the renal artery because the ultrasound power intensity decreases as the square of the distance from the center if the barrel transducer element 66 is longer than the inner diameter of the artery. It is also desirable to provide for cooling of the barrel transducer element 66, since its efficiency is typically not more than about 40%. Cooling can be accomplished by allowing blood to flow past the transducer 52 or by providing cooling liquid such as saline or D5W, which can be closed or open irrigated.

The beam angle, BA, of a barrel shaped cylindrical transducer 52 will be normal to the axis of the cylinder defining the transducer element 66 and will diverge with a beam, DB, which has one angle in the plane which intersects the axis of the cylinder and a second angle in the plane perpendicular to the first plane. The angle (DB) in the first plane is similar to that calculated above. The angle in the second plane is related to the diameter of the barrel of the transducer element 66, but the effective diameter is only about half as wide because ultrasound cannot be transmitted much off the normal, which makes the beam divergence about twice as great.

For either of the ultrasonic transducers 66 shown in FIGS. 14 and 15, it is desirable to choose a transducer diameter based on the renal artery diameter, which is about 5 mm, and a separation between the transducer 66 and the artery wall. It is the desirable to choose the optimum frequency to minimize the beam divergence at the artery wall location.

It is noted that the ultrasound units 50 shown in FIGS. 14 and 15 may be used with various stabilization arrangements, including balloons. In some embodiments, the transducer assembly 50 is enclosed within a balloon filled with saline, so that the balloon and shaft center the transducer 52 in the renal artery and the balloon stops blood flow so that less total power is required to heat the artery wall to ablate it. In other embodiments, the ultrasound units 50 shown in FIGS. 14 and 15 may be adapted to travel along a spiral rail supported by a shaft, such as is shown in FIG. 9, and may further travel within a filled balloon as shown and described with reference to FIG. 10.

Figure 16:
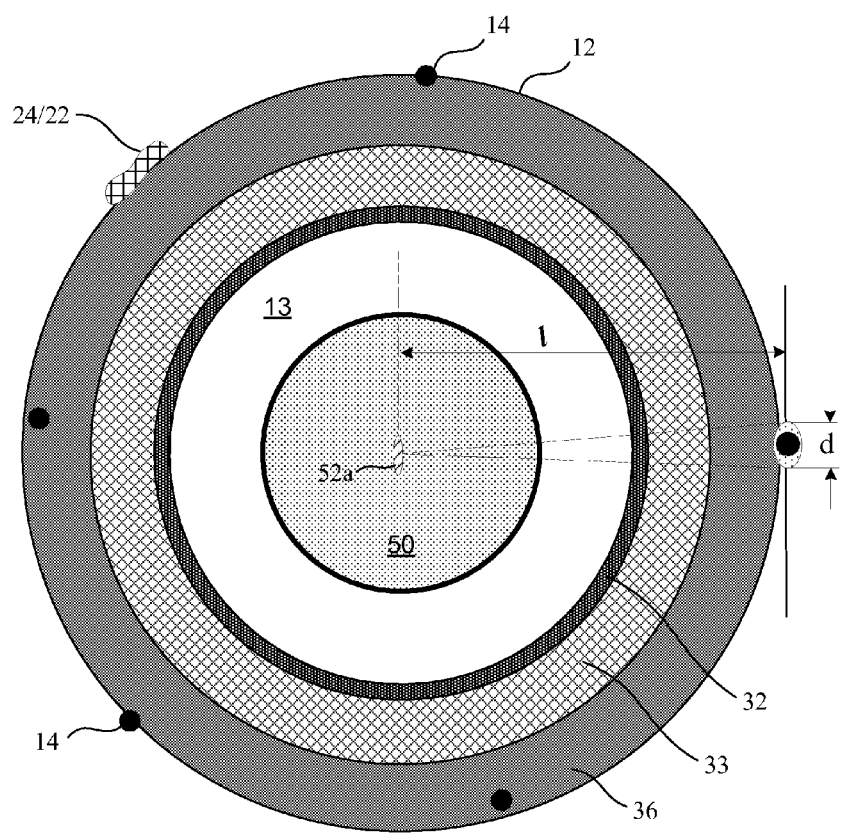
FIG. 16 is an exaggerated sectional view of a renal artery and an acoustic energy beam emitted from a focusing arrangement of an ultrasound unit positioned within a lumen of the renal artery in accordance with embodiments of the invention.

FIG. 16 is an exaggerated sectional view of a renal artery 12 and an ultrasonic beam emitted from an ultrasonic emitter 52a of an ultrasound unit 50 positioned within a lumen 13 of the renal artery 12. In this illustrative embodiment, the ultrasonic emitter 52a is configured to focus acoustic energy at a volume of tissue of the adventitia 36 proximate the outer wall of the renal artery 12 that includes a renal nerve 14.

As previously discussed, the ultrasound unit 50 may be operated to scan the adventitia 36 and vasa vasorum for renal nerves 14 and ganglia 24/22 using relatively low power acoustic energy. The ultrasound unit 50 may also be operated to deliver relatively high power acoustic energy to create lesions that permanently disrupt the target renal nerve 14. Employment of an ultrasound unit 50 that includes a HIFU emitter 52a advantageously spares tissues of the intima 32 and media 33 from injury.

It is generally known that a typical renal artery of a human adult has a diameter of about 5 mm. Embodiments of ultrasonic emitter and lens arrangements described herein may be implemented to project acoustic energy to foci having a depth of focus ranging between about 1 mm to about 10 mm, which is sufficient to reach target tissues of the renal artery wall, including ganglia, and the vasa vasorum proximate the outer wall of the renal artery.

In various embodiments, an ultrasonic emitter 52a may be implemented to project acoustic energy to foci having a depth of focus that falls within a target range that encompasses the outer adventitial layers of the renal artery. In other embodiments, an ultrasonic emitter 52a may be implemented to project acoustic energy to foci having a depth of focus that falls within a target range that encompasses the outer adventitial layers of the renal artery and the vasa vasorum proximate the outer wall of the renal artery. It is understood that ultrasonic emitter and lens arrangements may be configured for projecting acoustic energy to foci having a depth of focus that falls within a target range that encompasses renal nerves of the renal artery's ostium and ganglia of the abdominal aorta.

According to various embodiments, a multiplicity of disparate ultrasonic emitter and/or lens arrangements may be used to project acoustic energy to multiple foci having different depths of focus. Particular ones of the multiplicity of arrangements may be selectively operated for scanning and/or ablating at different tissue depths. For example, scanning at different depths within the outer renal artery wall and adjacent vasa vasorum can be performed to locate target tissue that includes one or both of renal nerves and ganglia. After determining the target tissue location and depth, which may alternatively be accomplished using a separate internal or external imager, a selected one or more of the ultrasonic emitter and/or lens arrangements may be used to ablate the target tissue at the determined depth.

Figure 17:
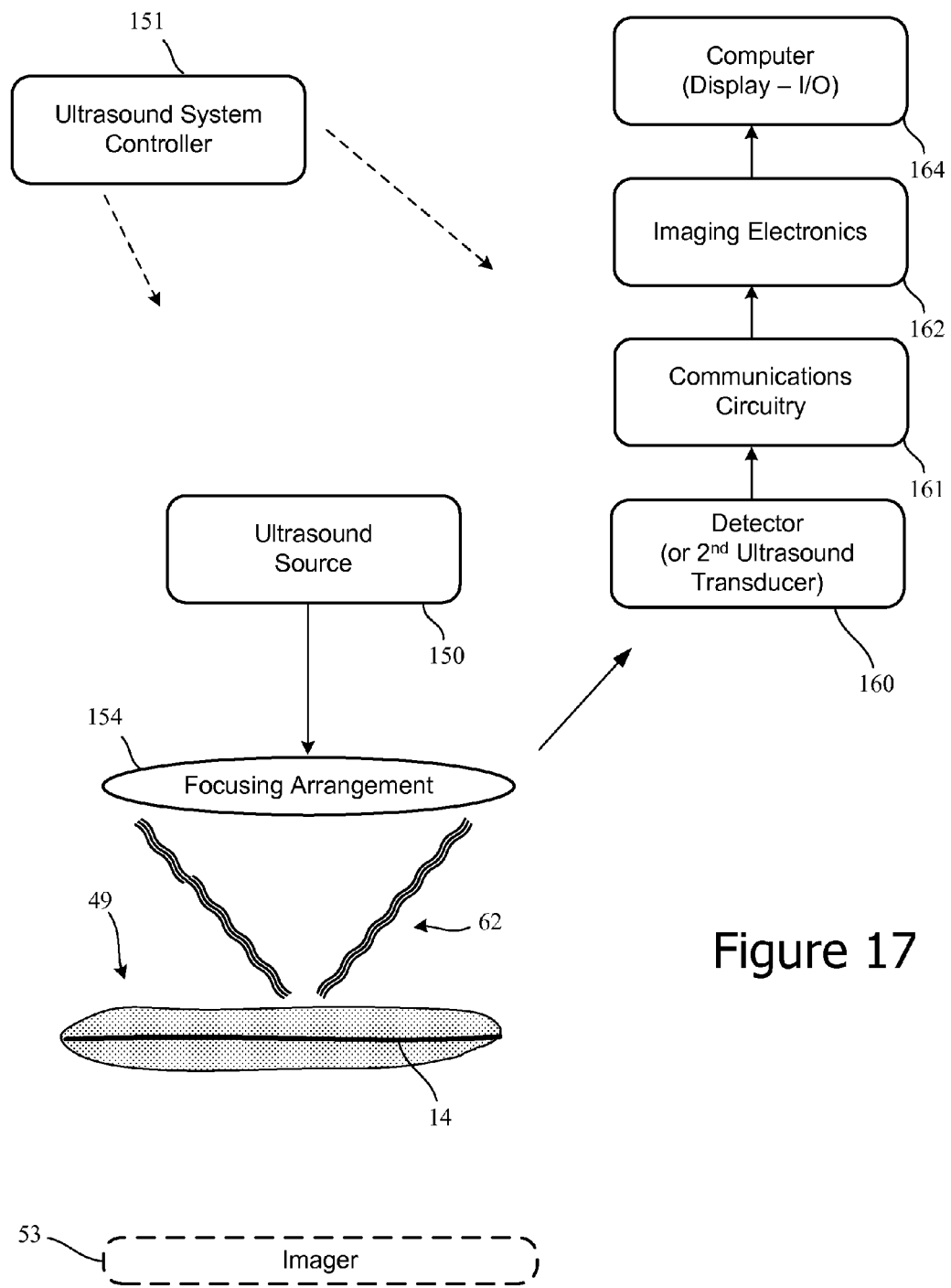
FIG. 17 shows an ultrasound delivery apparatus which includes an ultrasonic source, focusing arrangement, detector, imaging electronics, and computer system for processing and displaying ultrasonic imaging data in accordance with embodiments of the invention.

FIG. 17 illustrates an embodiment of an ultrasound system for denervating and optionally scanning innervated vasculature that contributes to renal sympathetic nerve activity in accordance with the invention. The ultrasound system shown in FIG. 17 includes a controller 151 configured to execute program instructions for controlling components and operations of the ultrasound system. The ultrasound system includes an ultrasound source 150 that generates acoustic energy having desired characteristics, such as desired frequency, intensity, beam pattern, and penetration depth characteristics. In some embodiments, the ultrasound source 150 is configured to generate a continuous wave (CW) acoustic beam. In other embodiments, the ultrasonic source 150 is configured to generate high intensity, low duty cycle pulses of acoustic energy.

The ultrasound delivery apparatus shown in FIG. 17 can be operated in a scanning or imaging mode, an ultrasonic denervation therapy mode, or both (sequentially or concurrently). In some embodiments, it may be desirable to incorporate a separate ultrasound delivery apparatus for each of a scanning or imaging mode and an ultrasonic denervation therapy mode.

According to various embodiments, acoustic energy produced by the ultrasonic source 150 is directed to a focusing arrangement 154. The focusing arrangement 154 may include one or more acoustic lenses for shaping and directing acoustic energy received from the ultrasonic source 150 to target tissue 49, such as renal artery tissue which includes a renal nerve 14. The acoustic energy exiting the focusing arrangement 154 and penetrating the target tissue 49 is preferably a focused ultrasonic beam 62 of sufficient intensity to permanently disrupt renal nerves 14 included in the target tissue 49. An imager 53 (external or internal) is preferably used to facilitate positioning of an ultrasound unit of the ultrasound delivery apparatus, and may also be used to determine or adjust various operating parameters, such as acoustic energy intensity, duty cycle, frequency, beam shape, beam direction, axial depth, and longitudinal resolution, for example.

In some embodiments, target renal artery tissue 49 can be heated using focused acoustic energy 62, and, if the artery wall tissue temperature exceeds 50° C., the tissue can be killed. However, the target tissue 49 will not be physically and permanently disrupted until the temperature of the target tissue 49 exceeds about 65° C., where the collagen reforms. With focused acoustic energy beams 62, a small focus can be achieved deep in target tissues 49, such as a focal region or volume within the adventitia tunica or vasa vasorum that includes a renal nerve or ganglion. When the temperature within the target tissue 49 reaches a sufficient level (e.g., >65° C.), the target tissue 49 is thermally coagulated (e.g., coagulative necrosis). By focusing at more than one tissue location or by scanning the focused beam, a volume of target tissue can be thermally ablated.

Other embodiments of the invention are directed to an ultrasound source 150 and a focusing arrangement 154 configured for operation in a cavitation ablation mode. Operating the ultrasound source 150 and focusing arrangement 154 in a cavitation ablation mode, for example, is preferably accomplished by transmitting a string of high intensity, low duty cycle acoustic energy pulses into the target tissue 49. Embodiments of the invention are also directed to an ultrasound source 150 and focusing arrangement 154 that is selectively operable in a cavitation ablation mode and a scan mode, allowing the ultrasound unit to locate target renal artery tissue in one mode and then permanently disrupt renal nerve fibers and ganglia within the target tissue in a second mode.

In accordance with other embodiments, acoustic energy produced by the ultrasonic source 150 may be used for imaging tissues of the renal and aortal vasculature. In ultrasonic imaging applications, the intensity of the acoustic energy is less than that required for ablation, and is preferably low enough to avoid thermal injury to scanned tissue.

In the embodiment shown in FIG. 17, acoustic energy backreflected from the target tissue 49 is received at a detector 160. The detector 160 may be incorporated in the transducer of the ultrasound source 150 or in a separate detector component. The detector 160 typically converts received acoustic energy to an electrical signal, which is transmitted to imaging electronics 162 via communications circuitry 161. Imaging electronics 162 preferably implements one or more known techniques for imaging scanned tissue 49 at various depths and transverse lengths or regions (e.g., focal volumes) using the backreflected acoustic energy. Output from the imaging electronics 162 is received by a computer 164 which preferably includes a display. Data and visual information concerning the scanning and ultrasonic denervation procedures are preferably presented on the display. The computer 164 may include an interface (I/O) for communicating with other systems and devices.

The controller 151 of the ultrasound system may be configured to generate a 2D image by controlling the sweep of the ultrasonic beam 62. The ultrasound source 150 may be swept mechanically, such as by rotating or swinging. In another approach, a 1D phased array ultrasound source 150 may be used to sweep the ultrasonic beam 62 electronically. The received data is processed by the computer 164 and used to construct the image. This image is a 2D representation of a slice into the renal artery or abdominal aorta. 3D images can be generated in real-time by acquiring a series of adjacent 2D images, such as by using one or more 2D phased array ultrasonic transducers that sweep the ultrasonic beam 62.

The ultrasound system may be operated in one or more scanning modes. In an A-scan mode, for example, a single ultrasonic transducer is used to scan a line through the renal artery tissue with the echoes plotted on a display as a function of depth. In a B-scan mode, a linear array of ultrasonic transducers are used to simultaneously scan a plane through the renal artery tissue that can be viewed as a two-dimensional image on the display.

Figure 18A:
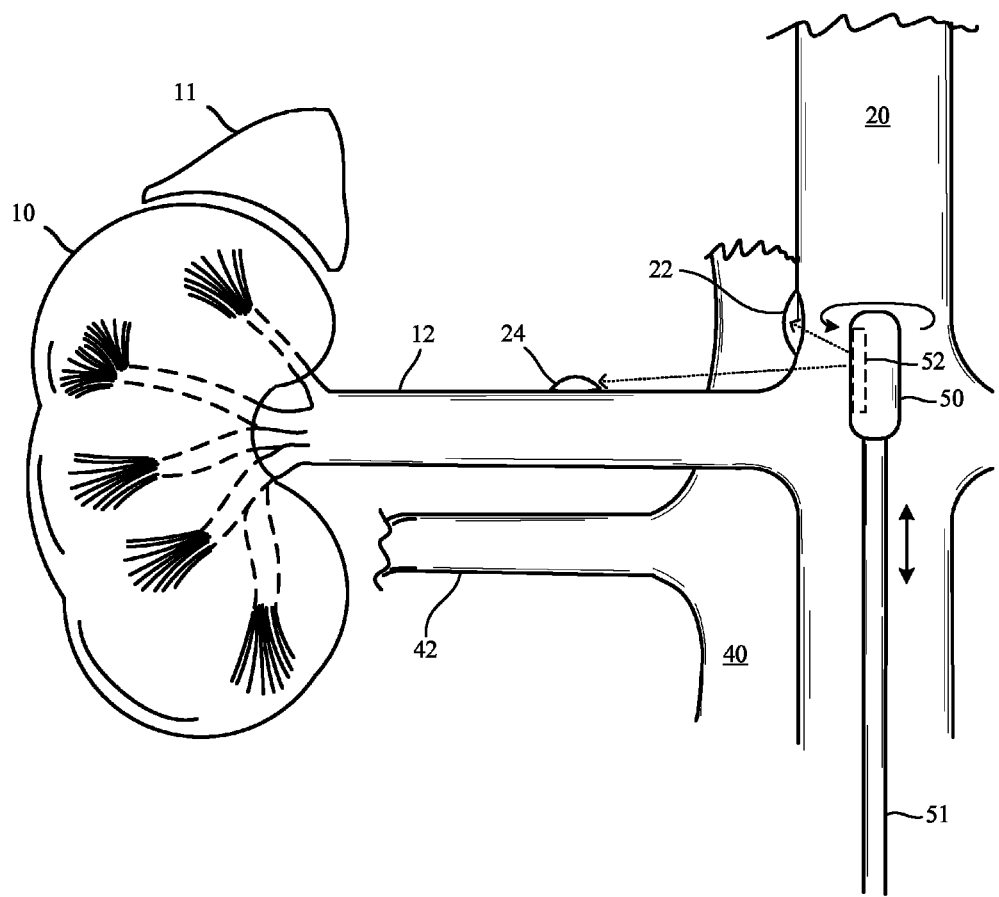
FIGS. 18A and 18B illustrate representative deployment configurations of a focused ultrasound catheter that can be operated for one or both of transvascular scanning and denervation of innervated vasculature in accordance with embodiments of the invention.
Figure 18B:
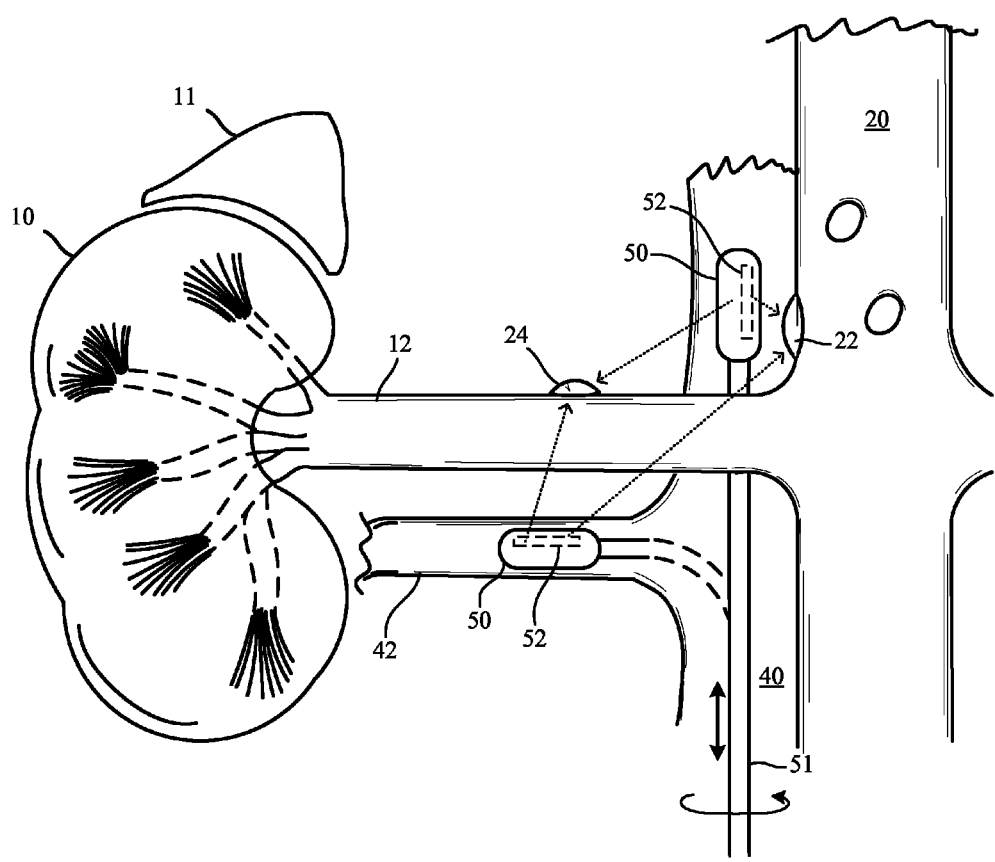

FIGS. 18A and 18B illustrate representative deployment configurations of a focused ultrasound catheter that can be operated for one or both of transvascular scanning and denervation of innervated vasculature in accordance with embodiments of the invention. In FIG. 18A, an ultrasound unit 50 is shown deployed in a patient's abdominal aorta 20 proximate a renal artery 12. In FIG. 18B, an ultrasound unit 50 is shown deployed in a patient's inferior vena cava 40 proximate a renal artery 12. In this position shown in FIG. 18B, the ultrasound unit 50 can be used to denervate the aorticorenal ganglion 22 and/or the renal ganglion 24.

When positioned within the patient's renal vein 42, as also shown in FIG. 18B, the ultrasound unit 50 can be used to denervate the aorticorenal ganglion and/or the renal ganglion. According to one procedure, the ultrasound unit 50 is moved to a renal vein location for denervating renal ganglia 24 of the renal artery 12, and moved to an inferior vena cava location for denervating ganglia of the abdominal aorta, such as the aorticorenal ganglion 22.

The ultrasound unit 50 includes an ultrasonic emitter 52 that can be operated in a denervation mode and, optionally, a scanning mode. In this representative illustration, the ultrasonic emitter 52 is operated in a scan mode to aid in locating target tissue, such as aorticorenal ganglion 22 and renal ganglion 24.

After locating the target tissue, the ultrasonic emitter 52 or another imaging device (external or internal) is used to determine the range to the target tissue. The ultrasonic emitter 52 is focused electronically (e.g., via a subaperture or electronic focus or steering technique) or mechanically at the target tissue based on the range information. Acoustic energy is transmitted to the target tissue sufficient to permanently denervate the target tissue, by use of thermal or cavitation ablation modes.

It is noted that an ultrasound unit 50 in accordance with various embodiments of the invention may incorporate multiple ultrasonic devices for purposes of imaging and/or ablating target tissue. Some of the ultrasonic devices, for example, can operate continuously in a scan mode, while other ultrasonic devices can be operated continuously, intermittently, or sequentially in an ablation mode.

Figure 19:
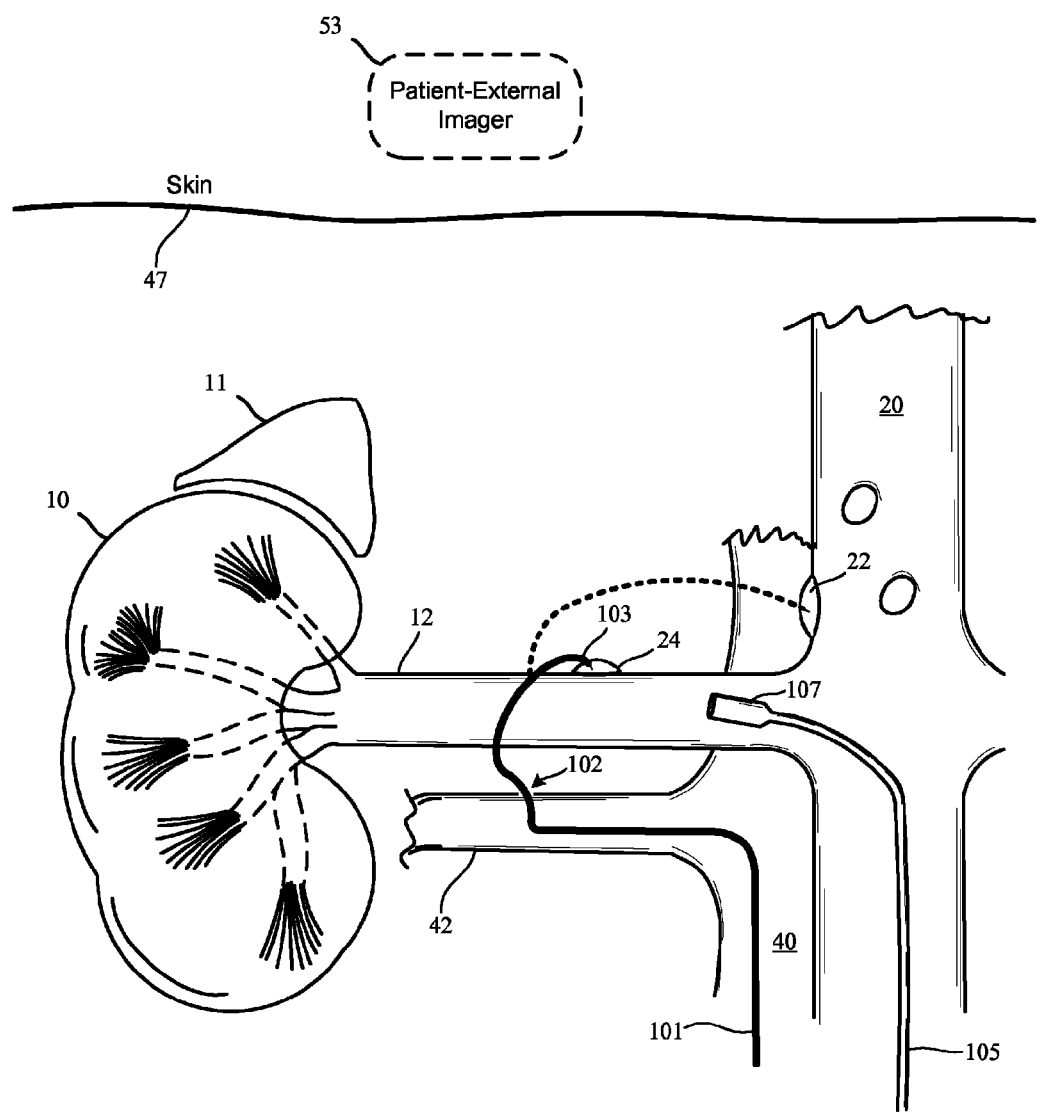
FIG. 19 illustrates an apparatus for facilitating guided delivery of an ablation agent to ganglia that contribute to renal sympathetic nerve activity in accordance with embodiments of the invention.

FIG. 19 illustrates an apparatus for facilitating guided delivery of an ablation agent to ganglia that contribute to renal sympathetic nerve activity in accordance with embodiments of the invention. According to various embodiments, a delivery catheter 101 is used cooperatively with an imaging system to locate a target ganglion and deliver an ablation agent to the target ganglion. In FIG. 19, the delivery catheter 101 is configured for intra-to-extra vascular deployment, and the imaging system may include an intravascular imaging catheter 105 or an external imager 53 of a type previously described.

According to some embodiments, an intravascular imaging catheter 105 is delivered to a location within a patient's renal artery 12, typically accessed via the inferior abdominal aorta 20. The intravascular imaging catheter 105 preferably includes an imaging device 107, such as an IVUS device or other ultrasonic imaging device, or a laser imaging device, such as a laser transducer or other optical imaging device. With the imaging device 107 properly positioned in or proximate the renal artery 12, the delivery catheter 101 is advanced into the renal vein 42, typically accessed via the inferior vena cava 40. The delivery catheter 101 preferably includes a steering mechanism. Suitable steering mechanisms that can be incorporated in a delivery catheter 101 of the present invention include various mechanisms incorporated into known steerable guide catheters.

The delivery catheter 101 includes a tissue penetrating feature at its distal tip, such as tissue piercing tip 103, to aid in creating an access hole 102 in the renal vein 42. Alternatively, an energy source, for example radiofrequency or laser, may be applied at the catheter tip to assist in puncturing the wall of the renal vein 42. With aid from the imaging catheter 105 or external imager 53, the delivery catheter 101 is advanced through the access hole 102 and navigated around the exterior of the renal artery 12 to a location adjacent a target ganglion, such as a renal ganglion 24.

Using the tissue piercing tip 103, the delivery catheter 101 is forcibly advanced so that a portion of the distal tip of the delivery catheter 101 penetrates into the renal ganglion 24. An ablation agent is delivered to ganglion tissue via the delivery catheter 101. The ablation agent is preferably effective in killing nerve fibers of the renal ganglion 24, so that all renal sympathetic nerve activity associated with the renal ganglion 24 is permanently terminated.

In some embodiments, the delivery catheter 101 includes a lumen which is fluidly coupled to a distal port and a proximal port of the delivery catheter 101. The proximal port is coupled to an ablation agent source, and the distal port is configured to dispense an ablation agent from the distal tip of the delivery catheter 101. In other embodiments, a cavity of the distal tip of the delivery catheter 101 contains an ablation agent, which may be a fluid, a solid, or a soluble mixture or matrix. The ablation agent may be eluted or otherwise communicated from the cavity of the distal tip of the delivery catheter 101 into the renal ganglion 24.

The delivery catheter 101 may be configured to deliver a variety of ablation agents via an ablation dispensing arrangement (e.g., lumen and port system, distal tip cavity). The ablation agent may take the form of a pharmacological agent or mixture of agents (e.g., a neurotoxin or venom), a thermal transfer fluid (hot or cold), or radioactive material or seeds (e.g., iodine-125 or palladium-103 for low dosage rate brachytherapy, iridium-192 for high dose rate brachytherapy). A variety of cryogens may be employed as ablation agents, including cold saline or cold saline and ethanol mixture, Freon or other fluorocarbon refrigerants, nitrous oxide, liquid nitrogen, and liquid carbon dioxide, for example. Alternatively, DC, AC, or RF electrical current may be dispensed from tip 103 via a lead that passes through lumen 102 to heat tissue or alter tissue sufficiently for ablation.

After delivering the ablation agent to the renal ganglion 24, the delivery catheter 101 can be navigated to another ganglion, such as the aorticorenal ganglion 22, the superior mesenteric ganglion, or the celiac ganglia or plexus. The imaging catheter 107 is preferably moved to an appropriate intravascular location to aid navigation and positioning of the delivery catheter 101, such as a location within the abdominal aorta 20 or renal vein 40.

One or more physiologic parameters can be monitored during the procedure to determine the effect of the ablation agent on the patient's renal sympathetic nerve activity. For example, an electrode arrangement may be situated in contact with the inner or outer wall of the renal artery 12 near opposing sides of the renal ganglion 24. The electrode arrangement may be configured to measure nerve impulses transmitted along renal nerve fibers that couple to or pass through the renal ganglion 24. By way of further example, one or more physiological parameters that are sensitive to changes in renal sympathetic nerve activity may be monitored, and the efficacy of the ablation agent at the renal ganglion 24 may be determined based on measured changes in the physiological parameter(s). Suitable apparatuses for these purposes are disclosed in commonly owned U.S. Patent Publication No. 2008/0234780 and in U.S. Pat. No. 6,978,174, which are incorporated herein by reference.

It is noted that marker bands can be placed on one or multiple parts of the catheter 105 and/or 101 to enable visualization during the delivery, imaging, and/or denervation procedures. The marker bands may be solid or split bands of platinum or other radiopaque metal, for example.

Figure 20:
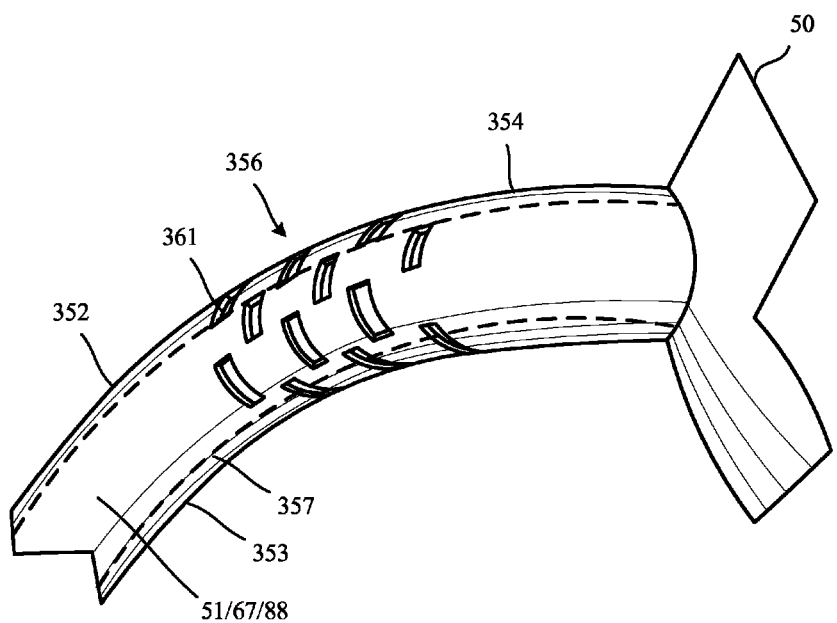
FIG. 20 shows a hinge mechanism that can be built into a catheter or other elongated member to enhance access to the renal artery and other vasculature in accordance with embodiments of the invention.

Referring now to FIG. 20, a catheter 51 to which an ultrasound unit 50 of the present invention is connected may incorporate a hinge mechanism 356 built into the catheter 51 proximate the ultrasound unit 50. The hinge mechanism 356 may be built into other elongated intravascular device embodiments of the disclosure, such as shaft 67 and shaft 88 of balloons 64 shown in FIGS. 8-11, respectively. The hinge mechanism 356 is constructed to enhance user manipulation of the catheter 51 when navigating around a nearly 90 degree turn from the abdominal aorta into the renal artery. It is understood that one or more hinge mechanisms 356 may be built into other catheters and sheaths that may be used to facilitate access to the renal artery via the abdominal aorta. For example, a delivery sheath or guide catheter that is used to provide renal artery access for a catheter 51 of a type described herein may incorporate one or more hinge mechanisms 356.

FIG. 20 illustrates a portion of the catheter 51 that incorporates a hinge mechanism 356 in accordance with embodiments of the invention. The hinge mechanism 356 is provided at a location of the catheter 51 between a proximal section 352 and a distal section 354 of the catheter's shaft. The hinge mechanism 356 is preferably situated near the proximal section of the ultrasound unit 50. According to various embodiments, the hinge mechanism 356 comprises a slotted tube arrangement that is configured to provide a flexible hinge point of the catheter's shaft proximate the ultrasound unit 50.

The catheter's shaft may be formed to include an elongate core member 357 and a tubular member 353 disposed about a portion of the core member 357. The tubular member 353 may have a plurality of slots 361 formed therein. The slotted hinge region 356 of the catheter's shaft may be configured to have a preferential bending direction.

For example, the tubular member 352 may have a plurality of slots 361 that are formed by making a pair of cuts into the wall of tubular member 361 that originate from opposite sides of tubular member 353, producing a lattice region of greater flexibility relative to the proximal and distal sections 352, 354 of the catheter's shaft. The thickness of the catheter wall at the hinge region 356 can be varied so that one side of the catheter wall is thicker than the opposite side. This difference in wall thickness alone (e.g., a hinge region devoid of slots) or in combination with a difference in slot (void) density at the hinge region 356 provides for a preferential bending direction of the distal portion of the catheter 51.

A hinge arrangement 356 constructed to provide for a preferential bending direction allows a physician to more easily and safely navigate the ultrasound unit 50 to make the near 90 degree turn into the renal artery from the abdominal aorta, for example. One or more marker bands may be incorporated at the hinge region 356 to provide visualization of this region of the catheter's shaft during deployment. Details of useful hinge arrangements that can be incorporated into embodiments of a catheter 51 of the present invention or other component that facilitates access to the renal artery/vein from the abdominal aorta are disclosed in U.S. Patent Publication Nos. 2008/0021408 and 2009/0043372, which are incorporated herein by reference. It is noted that the catheter 51 may incorporate a steering mechanism in addition to, or exclusion of, a hinge arrangement 356. Known steering mechanisms incorporated into steerable guide catheters may be incorporated in various embodiments of a catheter 51 of the present invention.

The discussion provided herein concerning degrees of induced renal nerve damage, temperature ranges, amount of energy delivered into target tissue, and other embodiment details presented in this disclosure are provided for non-limiting illustrative purposes. Actual therapeutic parameters associated with the denervation apparatuses and methodologies may vary somewhat or significantly from those described herein, and be impacted by a number of factors, including patient-specific factors (e.g., the patient's unique renal vasculature and sympathetic nervous system characteristics), refractoriness to drugs impacting renal function, type and technology of the therapy device(s), therapy duration and frequency, use of a single therapy device or multiplicity of therapy devices (in sequential or concurrent use), structural characteristics of the therapy device(s) employed, and other implementation and physiologic particulars, among others.

The foregoing description of the various embodiments of the invention has been presented for the purposes of illustration and description. It is not intended to be exhaustive or to limit the invention to the precise form disclosed. Many modifications and variations are possible in light of the above teaching. For example, the devices and techniques disclosed herein may be employed in vasculature of the body other than renal vasculature, such as coronary and peripheral vessels and structures. By way of further example, embodiments of an ultrasonic denervation unit may be implemented for chronic use, and structures other than a catheter, such as a stent, may be used to maintain positioning of the ultrasonic denervation unit within the renal artery or other vessel. It is intended that the scope of the invention be limited not by this detailed description, but rather by the claims appended hereto.

What is claimed is:

1. An apparatus, comprising:
   a first catheter including a central shaft and an inflatable balloon, the first catheter configured for deployment within a vessel proximate innervated tissue that contributes to renal sympathetic nerve activity;
   a second catheter slidable relative to the first catheter;
   a spiral rail mounted on an outer surface of the central shaft adjacent a distal end of the central shaft within an interior volume of the inflatable balloon;
   an acoustic transducer provided at the distal end of the second catheter and dimensioned for deployment within the vessel proximate the innervated tissue, wherein the second catheter includes a keyed channel member that is disposed around an outer surface of the spiral rail such that the acoustic transducer is translated along a helical path as the acoustic transducer is distally advanced or proximally retracted;
   a focusing arrangement configured to focus acoustic energy outwardly beyond an inner wall of the vessel and into the innervated tissue at or proximate an outer wall of the vessel; and
   a controller configured to control the acoustic transducer for at least one of scanning tissue and ablating the innervated tissue.

2. The apparatus of claim 1, wherein the controller is configured to control the acoustic transducer to selectively scan tissue and ablate the innervated tissue.

3. The apparatus of claim 1, wherein the acoustic transducer comprises an acoustic phased array transducer, the phased array transducer comprising:
   a plurality of acoustic elements; and
   driver electronics coupled to the acoustic elements;
   further wherein the controller is coupled to the driver electronics and configured to control activation of each of the acoustic elements of the phased array transducer for at least one of scanning tissue and ablating the innervated tissue.

4. The apparatus of claim 3, wherein the controller is configured to control activation of the acoustic elements of the phased array transducer for selectively scanning tissue and ablating the innervated tissue.

5. The apparatus of claim 1, wherein the acoustic transducer comprises a high-intensity focused ultrasound (HIFU) transducer.

6. The apparatus of claim 1, wherein the acoustic transducer comprises a linear phased array transducer.

7. The apparatus of claim 1, wherein the acoustic transducer comprises a curvilinear or a convex sector phased array transducer.

8. The apparatus of claim 1, wherein:
   the acoustic transducer comprises an acoustic phased array transducer; and
   the controller is configured to electronically adjust a focal length of the phased array transducer consistent with a distance between the phased array transducer and the innervated tissue.

9. The apparatus of claim 1, wherein the acoustic transducer and focusing arrangement cooperate to focus acoustic energy at foci at a desired depth within the innervated tissue of sufficient intensity to ablate the innervated tissue while negligibly injuring inner wall tissue of the vessel.

10. The apparatus of claim 1, wherein the acoustic transducer and focusing arrangement cooperate to focus acoustic energy at foci of spherical or cylindrical geometries at a desired depth within the innervated tissue in each of a first mode and a second mode, the first mode associated with acoustic energy of an intensity for scanning innervated tissue, and the second mode associated with acoustic energy of an intensity for ablating the innervated tissue.

11. The apparatus of claim 1, wherein the acoustic transducer is configured to generate an acoustic power level corresponding to focal peak intensities equal to or greater than about 2000 W/cm2 in the innervated tissue.

12. The apparatus of claim 1, wherein the acoustic transducer is configured for high intensity focused ultrasound operation in a cavitation ablation mode that produces bubbles within the innervated tissue that work to mechanically disrupt nerve fibers and ganglia included within the innervated tissue upon bursting.

13. The apparatus of claim 1, wherein the inflatable balloon is configured to receive a liquid that provides good acoustic coupling between the acoustic transducer and a wall of the balloon.

14. The apparatus of claim 1, wherein the inflatable balloon is configured to facilitate cooling of an inner wall of the vessel by one or both of a blood perfusion arrangement or an arrangement for receiving a thermal transfer fluid.

15. The apparatus of claim 1, wherein the keyed channel member is keyed with the spiral rail.

16. The apparatus of claim 1, wherein the keyed channel member captures the spiral rail.

17. The apparatus of claim 1, wherein the keyed channel member supports the acoustic transducer.

18. The apparatus of claim 1, wherein the keyed channel member is attached to the acoustic transducer.

* * * * *